United States Patent
Griffin et al.

(10) Patent No.: US 6,303,618 B1
(45) Date of Patent: Oct. 16, 2001

(54) CYCLIN DEPENDENT KINASE INHIBITING PURINE DERIVATIVES

(75) Inventors: Roger J Griffin, Northumberland; Alan H Calvert; Nicola J Curtin, both of Tyne & Wear; David R Newell, Northumberland; Bernard T Golding, Newcastle upon Tyne; Jane A Endicott; Martin E M Noble, both of Oxford; Francis T Boyle, Ends Congleton; Philip J Jewsbury, Cheshire, all of (GB)

(73) Assignee: Cancer Research Campaign Technology Limited, London (GB)

( * ) Notice: Subject to any disclaimer, the term of this patent is extended or adjusted under 35 U.S.C. 154(b) by 0 days.

(21) Appl. No.: 09/481,708

(22) Filed: Jan. 12, 2000

Related U.S. Application Data

(63) Continuation of application No. PCT/GB98/02025, filed on Jul. 10, 1998.

(30) Foreign Application Priority Data

Jul. 12, 1997 (GB) .................................................. 9714603
Mar. 28, 1998 (GB) .................................................. 9806743

(51) Int. Cl.$^7$ ......................... A61K 31/52; C07D 473/02
(52) U.S. Cl. ......................... 514/262; 514/266; 544/264; 544/276; 544/277
(58) Field of Search .................................. 514/262, 266; 544/264, 276, 277

(56) References Cited

U.S. PATENT DOCUMENTS

| | | | |
|---|---|---|---|
| 4,876,257 | * | 10/1989 | Hajos et al. . |
| 5,525,606 | * | 6/1996 | Moschel et al. . |
| 5,866,702 | * | 2/1999 | Mackman et al. . |

FOREIGN PATENT DOCUMENTS

| | | |
|---|---|---|
| 0 331 511 | 9/1989 | (EP) . |
| 0 458 618 | 11/1991 | (EP) . |
| 94/29312 A | 12/1994 | (WO) . |
| 96/04281 A | 2/1996 | (WO) . |
| 97/18212 A | 5/1997 | (WO) . |
| 97/20843 A | 6/1997 | (WO) . |
| 98 05335 A | 2/1998 | (WO) . |

OTHER PUBLICATIONS

Havlicek L et al: "Cytokinin–derived cyclin–dependent kinase inhibitors: synthesis and cdc2 inhibitory activity of olomoucine and related compounds" Journal of Medicinal Chemistry, vol. 40, No. 4, Feb. 14, 1997, pp. 408–412, XP002079219 cited in the application see the whole document.

Vesely J et al: " Inhibition of cyclin–dependent kinases by purine analogues" European Journal of Biochemistry, vol. 224, No. 2, Sep. 1, 1994, pp. 771–786, XP002009709 cited in the application see the whole document.

Chae M Y et al: "Substituted 06–benzylguanine–derivatives and their inactivation of human 06–alkylguanine–DNA alkyltransferase" Journal of Medicinal Chemistry, vol. 37, No. 3, Feb. 4, 1994, pp. 342–347, XP002079220 see the whole document.

Chae M Y et al: "8–Substituted 06–benzylguanine, substituted 6(4)–(benzyloxy)pyrimdine, and related derivatives as inactivators of human 06–alkylguanine–DNA alkyltransferase" Journal of Medicinal Chemistry, vol. 38, No. 2, Jan. 20, 1995, pp. 359–365, XP002079221 see the whole document.

Da Silva A et al: "Synthesis and biological activity of methyl–D–glucopyranoside derivatives of mercaptopurine and mercaptopyrimidine" European Journal of Medicinal Chemistry, vol. 29, No. 1, 1994, pp. 149–152 XP002079222 see the whole document.

Arris C et al: "Probing the active site and mechanism of action of 06–methylguanine–DNA methyltransferase with substrates analogues (06–substitued guanines)" Anti–Cancer Drug Design, vol. 9, No. 5, Oct. 1994, pp. 401–408, XP002079223 see the whole document.

Krenitsky T A et al : "Nucleosides of azathioprine and thiamprine as antiarthritics" Journal of Medicinal Chemistry, vol. 32, No. 7, Jul. 1989, pp. 1471–1475, XP002079224 see the whole document.

Huber G: "Zur Darstellung von 6–Alkoxy–Purinen" Chemische Berichte, vol. 90, No. 5, 1957, pp. 698–700, XP002079225 see page 699, compound V.

* cited by examiner

Primary Examiner—Taofiq A. Solola
(74) Attorney, Agent, or Firm—Pillsbury Winthrop LLP

(57) ABSTRACT

Method of treating a tumour or other cell proliferation disorder which comprises administering an effective amount of a purine compound which inhibits cyclic dependent kinase activity. Novel purine compounds and pharmaceutical compositions are also disclosed.

15 Claims, 2 Drawing Sheets

CYCLIN DEPENDENT KINASE INHIBITING PURINE DERIVATIVES

This application is a continuation of PCT/GB98/02025 filed Jul. 10, 1998.

FIELD OF THE INVENTION

The present invention relates to certain purine derivatives which show activity in biological systems as cyclin dependent kinase (CDK) inhibitors and which are accordingly of interest as potentially useful therapeutic agents that may be incorporated in pharmaceutical compositions or formulations for use in controlling or inhibiting cell growth or proliferation in mammals, for example in connection with antitumour or cancer treatment.

BACKGROUND

Cyclin dependent kinases (CDK's) are a family of enzymes which form complexes with other activating proteins known as cyclins to provide key regulatory factors that are involved in the control of growth and division in animal cells. More particularly, the progression of animal cells through the cell division cycle (G1, S, G2 and M phases) is regulated by the sequential formation, activation and subsequent inactivation of a series of CDK/cyclin dimer complexes which control passage past cell cycle checkpoints and transitions between successive phases of the cell cycle, with the CDK's acting as catalytic sub-units of the complexes.

There are in fact a number of different cyclin proteins which, like the different CDK's, form a somewhat loosely related family of CDK-activating proteins; different CDK/cyclin complexes function at different stages of the cell cycle with sequential increase and decrease in cyclin expression during the cell cycle and cyclin degradation during M phase usually being an important factor in determining orderly cell cycle progression. Thus, progression through G1 to S phase in mammalian cells is believed to be regulated primarily by cyclin dependent kinases CDK2, CDK3 and CDK4 (and possibly also CDK6 in some cells) in association with at least cyclins D and E, the complexes of CDK2 and CDK4 (and possibly CDK6) with D type cyclins in particular playing an important role in controlling progression through the G1 restriction point whilst the CDK2/cyclin E complexes are essential for bringing about the transition from G1 into S phase. Once S phase is entered it is believed that further progression and entry into G2 then requires activated complexes of CDK2 with another cyclin which is designated cyclin A, i.e. complexes CDK2/cyclin A. Finally, for the transition from G2 phase to M phase and initiation of mitosis, activated complexes of the cyclin dependent kinase designated CDK1 (also known as Cdc2) with a cyclin designated cyclin B (and also complexes of CDK1 with cyclin A) are required.

In general, control of the cell cycle and activity of CDK's involves a series of stimulatory and inhibitory phosphorylation and dephosphorylation reactions, and in exercising their regulatory functions the CDK/cyclin complexes when activated use ATP as a substrate to phosphorylate a variety of other substrate cell proteins, usually on serine and threonine groups thereof. Control of the cell cycle may also involve inhibitors of CDK/cyclin complexes which block the catalytic function of these enzymes so as to lead to arrest of the cell cycle. Certain natural inhibitors, such as for example the inhibitory proteins known as p16 and p21, can block cell cycle progression by binding selectively to CDK/cyclin complexes to inactivate the latter.

Control by inhibitors of CDK function may therefore provide a further mechanism for controlling cell cycle progression, and this has led to proposals for using CDK inhibitors as antiproliferative therapeutic agents, in antitumour therapy for example, for targeting abnormally proliferating cells and bringing about an arrest in cell cycle progression. This has seemed to be especially appropriate since it is known that severe disorders or irregularities in cell cycle progression frequently occur in human tumour cells, often accompanied by over-expression of CDK's and other proteins associated therewith. Also, compared to established cytologic antitumour drugs, the use of inhibitors of cell proliferation acting through CDK's would have the advantage of avoiding a direct interaction with DNA, thereby giving a reduced risk of secondary tumour development.

The potential therapeutic applications and other possible uses have accordingly led to a search for further chemical inhibitors of CDK's, especially selective inhibitors that may be suitable for pharmaceutical use. Inhibitory activity and selectivity of selected CDK/cyclin complexes is generally assayed by measuring the kinase activity in phosphorylating the protein histone H1 (one of the major protein constituents of chromatin which generally provides a good CDK substrate) in the presence of the suspected inhibitor under test. A number of compounds having potentially useful CDK inhibitory properties that have been identified in this way are described in a review article, of which the content is incorporated herein by reference entitled "Chemical inhibitors of cyclin-dependent kinases" by Laurent Meijer published in *Cell Biology* (Vol. 6), October 1996. Among the compounds referred to in the above-mentioned article is a potent CDK1 and CDK2 inhibiting adenine derivative 2-(2-hydroxyethylamino)-6-benzylamino-9-methyl-purine, named "olomoucine", and also a close analogue incorporating modifications at each of positions 2, 6 and 9, namely, 6-(benzylamino)-2(R)-[{1-(hydroxy-methyl)propyl}amino]-9-isopropylpurine. This latter compound is named "roscovitine" and is even more potent than olomoucine as a CDK inhibitor. The strong but selective CDK inhibitory properties of olomoucine were first described in a paper by J. Vesely et al entitled "Inhibition of cyclin-dependent kinases by purine analogues", *Eur. J. Biochem.* 224, 771–786 (1994), and further studies on CDK inhibitory properties of a range of purine compounds in the form of adenine derivatives, including olomoucine and roscovitine, are reported and discussed in a paper by L. Havlicek et al entitled "Cytokinin-Derived Cyclin-Dependent Kinase Inhibitors: Synthesis and cdc2 Inhibitory Activity of Olomoucine and Related Compounds" *J. Med. Chem.* (1997) 40, 408–412. Again, the content of these publications is to be regarded as being incorporated herein by reference.

The inhibitory activity of both olomoucine and roscovitine has been shown to result from these compounds acting as competitive inhibitors for ATP binding. It may be noted that olomoucine at least is reported as having a total lack of inhibitory activity in relation to many common kinases other than CDK's. Selectivity is further manifest by the fact that both olomoucine and roscovitine inhibit activity of CDK1, CDK2 and CDK5, but neither has been found to be active against CDK4 or CDK6.

Olomoucine in particular has been regarded as providing a lead compound for helping to identify and design further purine based CDK inhibitors, and based on structure/activity studies it was suggested in the above-mentioned paper of Vesely et al that N9 substitution by a hydrophobic residue such as methyl, 2-hydroxyethyl or isopropyl was important, e.g. to provide a direct hydrophobic interaction with the CDK, and that a side chain at C2 appeared to be essential. Similarly, in the paper of Havlicek et al, apart from observing that for CDK inhibitory activity the 1 and 7 positions, and possibly the 3 position, of the purine ring must remain free to permit hydrogen bonding, it was also stated that a polar side chain at position 2 appears to be essential and that N9 substitution by a hydrophobic residue is also probably important for positive binding. Positions 2, 6 and 9 in the purine ring were identified as being the positions which control binding to CDK1.

In the review article of Meijer, it is also mentioned that as a result of crystallization of CDK—inhibitor complexes, and in particular co-crystallization studies with CDK2, it has been found that inhibitors such as olomoucine and roscovitine localize in the ATP binding pocket which is located in the cleft between the small and large lobes of the CDK protein molecule, and that specificity was probably provided by portions of the inhibitor molecules interacting with the kinases outside the ATP binding sites.

SUMMARY OF THE INVENTION

The present invention has developed from an observation made in the course of testing various guanine derivatives for activity as inhibitors of the DNA repair protein $O^6$-methylguanine DNA-methyltransferase (MGMT) when it was found unexpectedly that although the compound $O^6$-cyclohexylmethylguanine had very little activity as a MGMT inhibitor, it was nonetheless cytotoxic and showed very high inhibitory activity, comparable to that of olomoucine, against CDK1(cdc2)/cyclin B complexes. This was particularly surprising against the background discussed above in relation to olomoucine given that this guanine compound has no substituents at either the 2-$NH_2$ position or the 9 position in the purine ring and that the replacement of the 6-NH by 6-O made the compound less like ATP with which olomoucine at least is believed to compete for binding sites.

Subsequently, other guanine derivatives have been identified, more closely related to $O^6$-cyclohexylmethylguanine than to compounds such as olomoucine and roscovitine, which show significant CDK inhibitory activity, and crystallographic studies have revealed that complexes of CDK2 (homologous with CDK1, at least in respect of the catalytic binding site) with guanine derivatives such as $O^6$-cyclohexylmethylguanine and $O^6$-cyclohex-1-enylmethylguanine bind together in a different manner from complexes of CDK2 with olomoucine.

Figure 2:
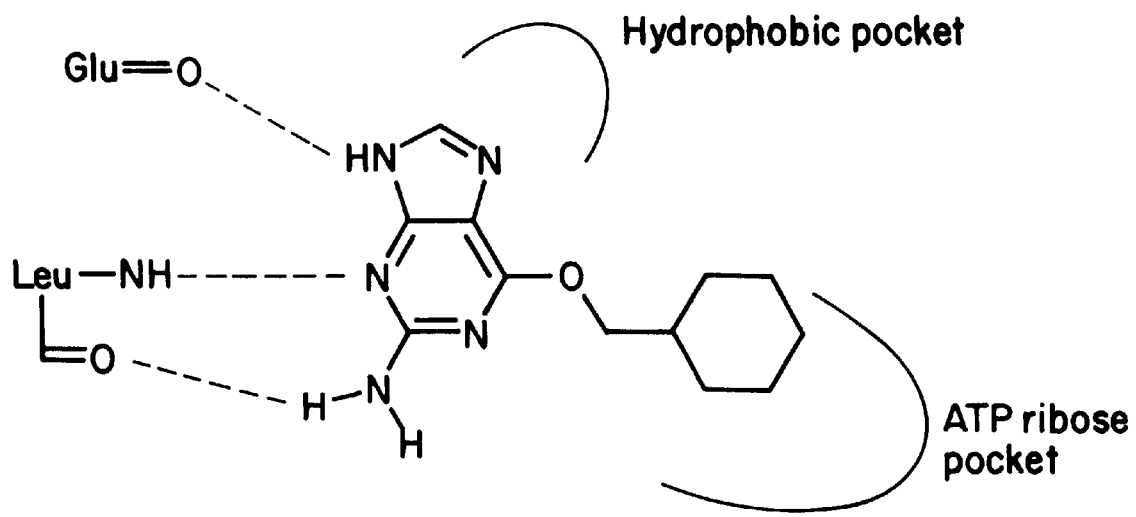
FIG. 2 is a similar diagram indicating the manner in which the compound $O^6$-cyclohexylmethylguanine has been found to bind to CDK2.
Figure 3:
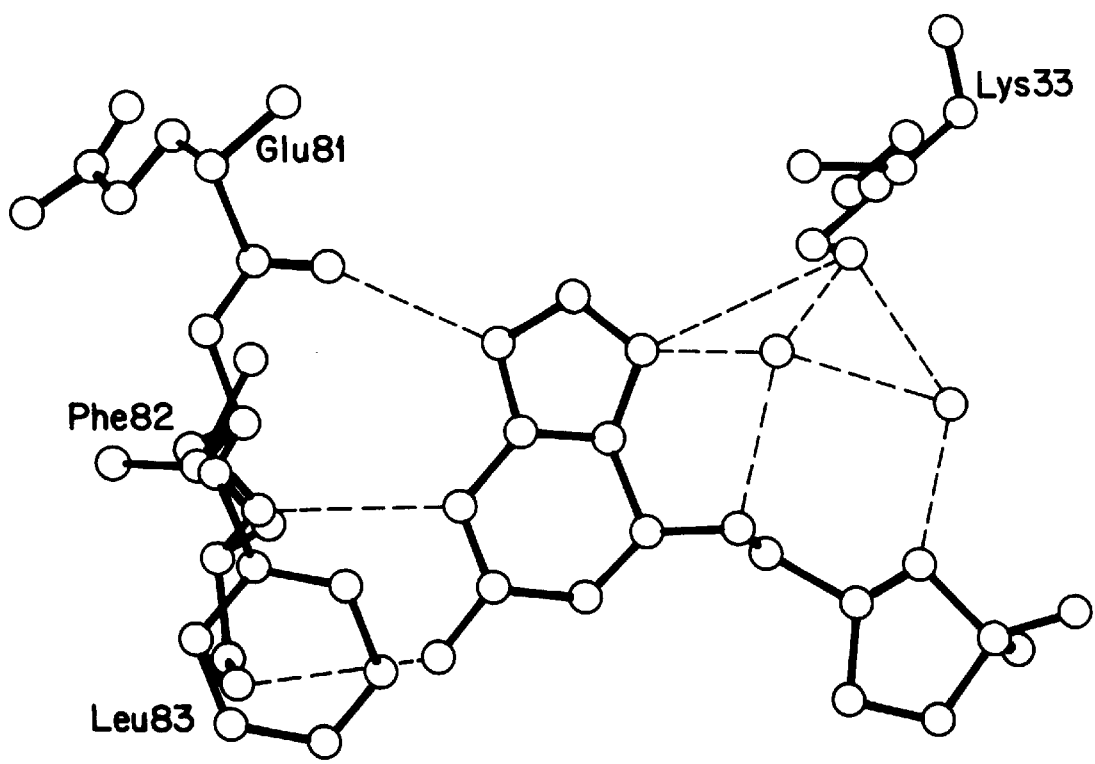
FIG. 3 is a diagram representing a crystal structure showing the manner in which the R enantiomeric form of the compound $O^6$-(2,2-dimethyl- 1,3dioxolane-4-methoxy) guanine has been found to bind to CDK2.

Whereas with olomoucine it is the polar side chain on N2 of the purine ring that seats within the ATP ribose binding pocket of the CDK2 protein, and the N9 methyl substituent engages a separate hydrophobic specificity pocket, with N7 and 6-NH being involved in hydrogen bonding to the protein, in the binding mode illustrated in FIG. 2 it is the cycloalkyl ring of the substituent at the 6-position that seats in the ATP ribose binding pocket while hydrogen bond links are formed to N9, N3 and 2-NH. In other words, the orientation as compared with the binding of olomoucine is completely reversed. A similar situation obtains with the binding mode illustrated in FIG. 3 where the involvement of some water molecules is also indicated.

It will accordingly be clear that conclusions reached in respect of structure/activity relationships in the adenine series of compounds exemplified by olomoucine and roscovitine are likely no longer to be valid for all purine derivatives, especially guanine derivatives.

Figure 1:
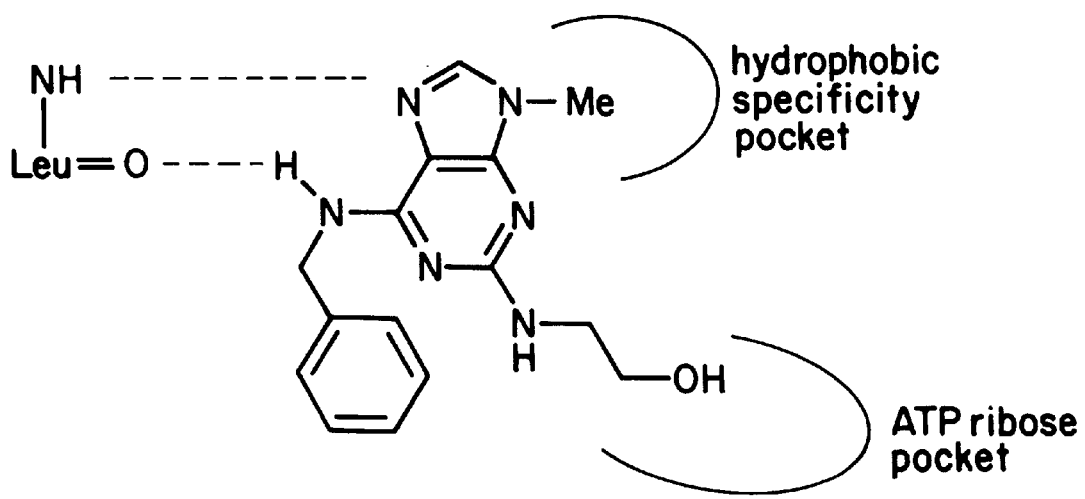
FIG. 1 is a diagram indicating the manner in which olomoucine binds to CDK2.

The compounds with which the present invention is concerned are primarily purine compounds which have inhibitory activity in respect of at least some CDK's and which bind in the manner shown in FIG. 2 (or FIG. 3) rather than in the manner shown in FIG. 1. Although some of these compounds are already known per se, they are not known in a capacity as CDK inhibitors. In some cases this inhibitory activity has been found to have a selectivity towards different CDK's which is notably different from that of olomoucine, and the present invention has in effect identified a new class of CDK inhibitors and has considerably enlarged the range of compounds available for use as CDK inhibitors.

In one aspect the present invention accordingly provides pharmaceutical compositions for treatment of cell proliferation disorders in mammals, for example tumors said compositions containing as the active ingredient a CDK-inhibiting purine compound having the structural formula I below:

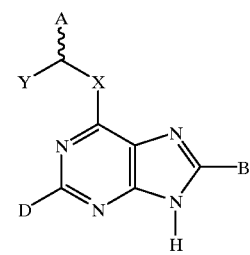

I where, in preferred embodiments,

X is O, S or $CHR_X$ where $R_x$ is H or $C_{1-4}$ alkyl;

D is H, halo or $NZ_1Z_2$ where $Z_1$ and $Z_2$ are each independently H or $C_{1-4}$ alkyl or $C_{1-4}$ hydroxyalkyl;

A is selected from H, $C_{1-4}$ alkyl, $C_{1-4}$ alkoxy, hydroxy, $CH_2(CH_2)_nOH$ (n=1–4, and $NR_{a1}R_{a2}$ where $R_{a1}$ and $R_{a2}$ are each independently H or $C_{1-4}$ alkyl;

B is selected from H, $C_{1-4}$ alkyl, $C_{1-4}$ alkoxy, $CF_3$, an optionally substituted aryl (e.g. phenyl) or an optionally substituted aralkyl (e.g. benzyl), and an hydroxy group that provides a C=O tautomer; and Y is or includes an optionally substituted 4- to 8-membered carbocyclic or heterocyclic ring.

In some cases, however, Y may comprise an optionally substituted linear or branched hydrocarbon chain, especially a chain containing a double band, e.g. an allyl derivative as hereinafter referred to.

So long as it is able to fit or seat in the ATP ribose binding pocket of a CDK protein and permit binding in the general manner depicted in FIG. 2 rather than FIG. 1, there is a wide range of substituents likely to be suitable for Y. In some cases, however, it may be helpful for Y to comprise a ring structure that includes polar hydroxyl substituents or the like.

In most embodiments Y will be a cycloalkane or cycloalkene ring, preferably a 5- or 6-membered ring having up to two double bonds. One or two carbon atoms in the ring may be replaced, however, by hetero atoms or groups, particularly O, S, NR' (where R' is H or $C_{1-4}$ alkyl) or, in a cycloalkene ring, —N=. Where the ring is substituted the substituent or each substituent (at any position) will preferably be selected from H, $C_{1-4}$ alkyl, OH, $C_{1-4}$ alkoxy, halogen, $CF_3$, CN, $N_3$ and $NR_{y1}R_{y2}$ where $R_{y1}$ and $R_{y2}$ are each independently H or $C_{1-4}$ alkyl. Moreover, in the case where there are two substituents on adjacent atoms of the ring, e.g. 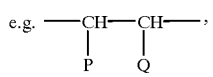

these substituents P and Q may be linked to form an additional fused ring structure, e.g. a 4-, 5- or 6-membered carbocyclic or heterocyclic ring. This additional ring structure may include for example up to two hetero atoms or groups such as O, S or NH, and it may also be substituted by one or more substituents, e.g. a $C_{1-4}$ alkyl group or groups or a phenyl or substituted phenyl group. In some embodiments, Y may also be adamantyl.

Examples of ring structures represented by Y include

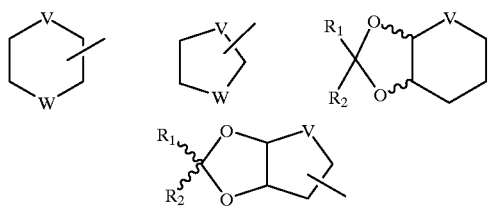

where V and W are each selected independently from

O, S, NR' (R' is H or $C_{1-4}$ alkyl)

and $CH_2$ (or =CH—); and $R_1$ and $R_2$ are each H or $C_{1-4}$ alkyl.

As indicated above, these ring structures can optionally bear substituents which may be the same or different and which may inter alia be selected from H, $C_{1-4}$ alkyl, $C_{1-4}$ alkoxy, —OH, $NR_{y1}R_{y2}$ (where $R_{y1}$ and $R_{y2}$ are each independently H or $C_{1-4}$ alkyl), $CF_3$, halogen, $N_3$, CN, optionally substituted aryl (e.g. phenyl), and optionally substituted aralkyl (e.g. benzyl). Also, as already indicated, it may be especially advantageous for the ring structure to have a plurality of polar substituents such as hydroxyl for example.

Some specific examples of the structures of potentially useful CDK inhibitory compounds in accordance with this invention include the following:

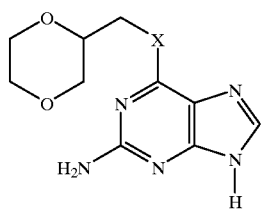

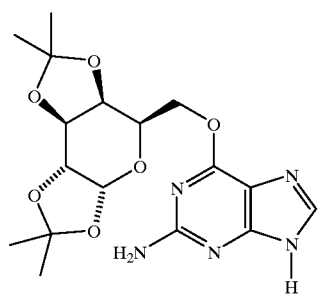

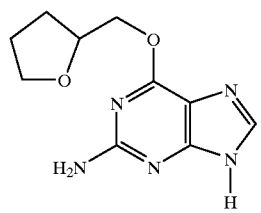

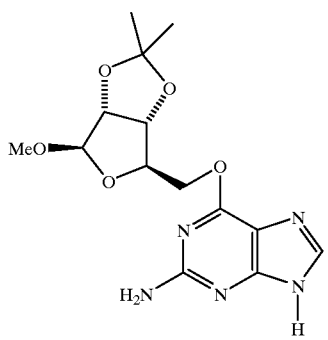

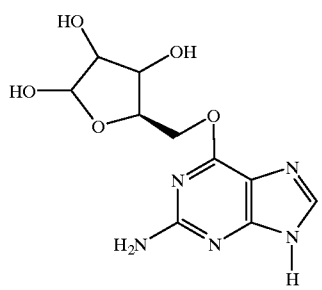

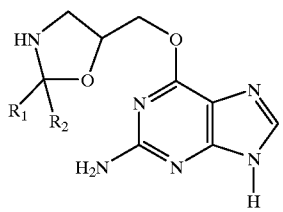

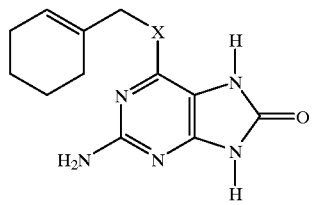

-continued

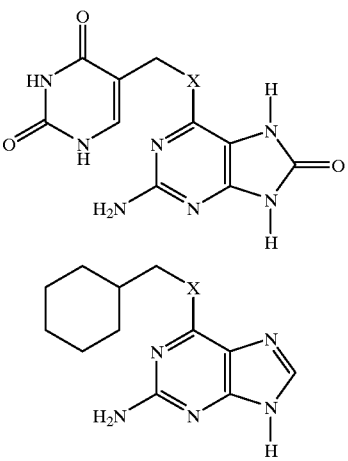

X = O or S
R₁ = H, CH₃ or C₂H₅
R₂ = H, CH₃ or C₂H₅

In general, the pharmaceutical compositions of this invention will contain an effective CDK-inhibiting non-toxic amount of the active purine compound, and will be formulated in accordance with any of the methods well known in the art of pharmacy for administration in any convenient manner, and may for example be presented in unit dosage form admixed with at least one other ingredient providing a compatible pharmaceutically acceptable additive, carrier, diluent or excipient.

It will be understood that where reference is made in this specification to compounds of formula I such reference should be construed as extending also to their pharmaceutically acceptable salts and to other pharmaceutically acceptable bioprecursors (pro-drug forms) where relevant. The term "pro-drug" is used in the present specification to denote modified forms or derivatives of a pharmacologically active compound which biodegrade in vivo and become converted into said active compound after administration, especially oral or intravenous administration, in the course of therapeutic treatment of a mammal. Such pro-drugs are commonly chosen because of an enhanced solubility in aqueous media which helps to overcome formulation problems, and also in some cases to give a relatively slow or controlled release of the active agent.

It should also be understood that where any of the compounds referred to can exist in more than one enantiomeric and/or diastereoisomeric form, all such forms, mixtures thereof, and their preparation and uses are within the scope of the invention. It should be noted, however, that stereochemical considerations are likely to be important and there may be considerable selectivity such that different enantiomers or diastereoisomers have significantly different inhibitory activity.

The invention also includes of course the use of the CDK inhibiting compounds referred to for the manufacture of medicaments or pharmaceutical compositions as referred to above, and it also includes the treatment of abnormal cellular proliferation disorders using such medicaments or pharmaceutical compositions.

Preferably, in compounds of structural formula I which are used in carrying out the invention, D will be an unsubstituted amino group —NH₂, and X will be O, although in some embodiments the amino group may be mono- or di-substituted, with a lower alkyl group for example.

Although it will usually be preferred that Y should comprise a saturated or partially saturated carbocyclic or heterocyclic ring structure, it should be recognised that in some cases Y may comprise an aromatic ring system (e.g. optionally substituted aryl or aralkyl), or even a linear or branched chain (preferably including a double bond as for example in allyl derivatives) and still provide compounds of interest as potentially selective CDK inhibitors that may be useful in the context of the present invention, especially insofar as they may be structured so as to bind with CDK's in substantially the same manner as depicted in FIG. 2.

Although a number of the CDK inhibitor compounds herein disclosed are already known per se as previously pointed out, some of the compounds are believed to be novel and to constitute new chemical entities. Examples of such novel compounds which have been made include $O^6$-Ribofuranosylguanine
2-amino-6-(2-tetrahydro-furanyl)-methyloxypurine
2-amino-6-adamantyl-methyloxypurine
$O^6$-Galactosylguanine
2-amino-6-(2-naphthyl)-methyloxypurine
2-amino-6-(2-tetrahydropyranyl)-methyloxypurine
2-amino-6-(1-naphthyl)-methyloxypurine
$O^6$-(2,2-Dimethyl-1,3-dioxolane-4-methoxy)guanine
$O^6$-(1,4-Dioxaspiro[4.5]decane-2-methoxy)guanine Examples of compounds which are at present especially preferred for use in carrying out the invention, and which include the most potent CDK inhibitors identified, at least when assayed in vitro against CDK1 and/or CDK2, are the following:

2-amino-6-(3-methyl-2-oxo)butyloxypurine ethylene acetal
2-amino-6-cyclohexyl-methyloxypurine
($O^6$-cyclohexylmethylguanine)
2-amino-6-cyclopentyl-methyloxypurine
($O^6$-cyclopentylmethylguanine)
2-amino-6-cyclohex-3-enylmethyloxypurine
2-amino-6-cyclopent-1-enylmethyloxypurine
($O^6$-Cyclopentenylmethylguanine)
2-amino-6-(1-cyclohexenyl)-methyloxypurine
($O^6$-Cyclohexenylmethylguanine)
2-amino-6-perillyloxymethylpurine Biological Activity Assays are available for testing the inhibitory activity of the compounds of interest against a range of CDK/cyclin complexes, including CDKI/cyclin A, CDK1/cyclin B, CDK1/cyclin F, CDK2/cyclin A, CDK2/cyclin E, CDK4/cyclin D, CDK5/35 and CDK6/cyclin D3, and it is of particular interest to note the selectivity of some of the compounds against different CDK's.

Test results showing CDK inhibitory activity values measured for some of the compounds that have been prepared are shown in Table 1 at the end of the present description. Where the compounds exist in different enantiomorphic forms, the assays have generally been carried out on racemic mixtures. Apart from reference compounds, the compounds listed are accompanied by an NU reference or identification code number. Table 1 includes the compounds which at present are the most preferred of those that have been prepared, although as yet not all have been fully tested. Four compounds, NU2036, NU2037, NU2038 and NU2051, are included in this Table 1 primarily to show how activity drastically diminishes if there are side chains at N9 or N7, or a halo substituent at C2.

As will be seen, in a number of cases the inhibitory assays have been carried out and data has been obtained in respect of CDK2 and/or CDK4. as well as in respect of CDK1. It is of some considerable importance to note that some of these compounds, unlike the previously known CDK inhibitors olomoucine and roscovitine, exhibit very significant selectivity as between CDK1 and CDK2. Also, some also exhibit significant activity against CDK4.

In general, the studies carried out fully support the belief that CDK inhibitory characteristics of compounds tested reflect an ability of these compounds to act as effective antitumour drugs.

The inhibition assays have been carried out using methods based on those described in the paper hereinbefore referred to of J. Vesely et al and in the paper of L. Azzi et al (1992) *Eur. J. Biochem.* 203, 353–360. By way of example, however, a typical protocol is summarised below.

CDK Assay Example

Reagents.

Buffer C (containing 60 mM b-glycerophosphate, 30 mM nitrophenyl phosphate, 25 mM MOPS pH 7.0, 5 mM EGTA, 15 mM $MgCl_2$, 1 MM $MgCl_2$ and 0.1 mM sodium orthovanadate) is made up as follows:

|  | FW | g/100 ml | Final conc |
|---|---|---|---|
| b-glycerophosphate (RT) | 216 | 1.3 | 60 mM |
| MOPS (RT) | 209.3 | 0.52 | 25 mM |
| EGTA (RT) | 380.4 | 0.19 | 5 mM |
| $MgCl_2$ (RT) | 203.4 | 0.305 | 15 mM |

First dissolve above ingredients in about 80 ml distilled water and pH to 7.0

Then add 1 ml 10 mM sodium orthovanadate (1.84 mg/ml—FW=183.9 RT)

final conc=0.1 mM cool to 4° C.

Then Add

| 4-nitrophenyl phosphate (−20° C.) | 279.2 | 1.112 | 30 mM |
|---|---|---|---|
| DTT (4° C.) | 154.2 | .0154 | 1 mM |

(Alternatively, make up 100 mM DTT (15.4 mg/ml) and store in 1.2 ml aliquots in freezer, thaw and add 1 ml to buffer, above)

Make up to 100 ml and store in 5 ml aliquots in freezer

Affinity purified p34 cdc2(CDK1)/cyclinB from M-phase starfish (*Marthasterias glacialis*) in 20% glycerol is stored at −80° C. in chest freezer 100 mM Olomoucine (Cat # LC-0-3590-M025 Alexis Co. Bingham Nottingham). FW=298.35 29.835 mg/ml=100 mM, 25 ml aliquots stored in freezer.

1% phosphoric acid (58.8 ml 85% phosphoric acid+4.942 litres water)

Make up the following on day of assay.

Histone H1 (type III-S (Sigma) 4° C.) 5 mg/ml in buffer C.

[$^{32}$P]ATP 75 mM: Make up using (multiples of) the following proportions:

2 ml [$^{32}$P]ATP (3000 Ci/mMol PB168 Amersham, stored in radioactive freezer)+7.5 ml 1 mM cold ATP (−20° C.) (0.551 mg/ml−200 ml aliquots stored in freezer)+ 90.5 ml buffer C Conc.=12.5 mM in final assay Assay Procedure DMSO cannot exceed 1% in the assay mixture. Inhibitors are added at 1/10 final assay volume and 10×final strength. DMSO stocks must therefore be diluted to 10×final desired concentration in $\leq$10% DMSO, $\geq$90% buffer C. Suggested concentration ranges=0, 1, 10, 100 mM so DMSO stocks of 0, 100, 1,000 and 10,000 mM are diluted 1/10 in buffer C before adding to assay.

Preparation:

Label set of 0.2 ml microtubes for assay (e.g. $A_0, A_1, A_{10}, A_{100}$) in suitable rack and another set of eppendorfs for drug dilution Label phosphocellulose filters in pencil (e.g. $A_0, A_1, A_{10}, A_{100}$) and fold longitudinally to make a "pitched roof"

Set up water bath at 30° C. containing second rack for microtubes

Set up beaker containing wire mesh insert and magnetic flea below mesh insert. together with 400 ml 1% phosphoric acid, on magnetic stirrer Reaction Mix:

All reagents (except DMSO stocks) should be kept on ice until assay initiated.

Place rack of assay tubes on ice

In each tube put:

16 ml buffer C 1 ml cdc2/cyclinB kinase 5 ml histone H1

3 ml inhibitor

Start reaction in each tube at 30 second intervals by adding 5 ml [$^{32}$P]ATP vortexing and placing in rack in waterbath at 30° C.

Terminate reaction after 10 min at 30 second intervals in tubes in same order by removing 25 ml reaction mix and spotting onto appropriately labelled filter, allowing to dry for 20–30 seconds and transferring to stirring 1% phosphoric acid.

Blank incubation is performed as above but without histone (add 5 ml buffer C instead) Washing blank is 5 ml ATP added directly to filter.

Wash filters 5–6 times 5 min each

Dry the filters on paper towel

Count in mini scintillation vials with 5 ml scintillant.

3×standards of 5 ml ATP counted also (375 pmoles ATP)

NB. The assay can be simplified by making up stock reaction mix as follows:

(1 part cdc2/cyclinB, 16 parts buffer C, 5 parts histone H1)×Number of assay tubes+1 and add 22 ml to each assay tube containing 3 ml buffer C±inhibitor. It is still necessary, however, to make up assay blank (i.e. without histone) separately.

DESCRIPTION OF ILLUSTRATIVE EXAMPLES

The following examples and description of stages in synthetic routes of preparation of various exemplary compounds of interest serve further to illustrate the present invention, but should not be construed in any way as a limitation thereof. Again, in many instances the compounds described are accompanied by an NU reference or identification code number.

The first two compounds of which the preparation is described, namely 2-amino-trimethylpurin-6-ylammonium chloride and 2-amino-6-(1,4-diazabicyclo[2,2,2]oct-1-yl) purinium chloride ("DABCO-purine") are intermediates used in the preparation of many of the other compounds subsequently described.

2-Amino-trimethylpurin-6-ylammonium chloride

Anhydrous trimethylamine was bubbled through a solution of 2-amino-6-chloropurine (10 g, 59 mmol) in anhydrous N,N-dimethylformamide (80 ml) for 30 min and the reaction stirred at room temperature for 12 h under a stream of nitrogen. The crude product was collected by filtration, dissolved in the minimum amount of cold water and the product precipitated out by the addition of acetone. The title compound was collected as a white solid (9.96 g, 74%)(m.p. 205–206° C.). (Found C, 41.8; H, 5.6; N, 36.9 $C_{10}H_{13}N_5O$ requires C, 42.1; H, 5.7; N, 36.8%). $\nu_{max}/cm^{-1}$ 3460 ($NH_2$), 3320 (NH), 1640 (C=C), 1570 (C=C); $\lambda_{max}$ ($CH_3OH$)/nm 316; $\delta_H$ (200 MHz, $d_6$-DMSO) 13.40 (1H, br s, NH), 8.35 (1H, s, C(8)H), 7.10 (2H, s, $NH_2$), 3.70 (9H, s, N($CH_3$)$_3$); $\delta_C$ (50.3 MHz, $d_6$-DMSO) 159.5 (C6), 154.9 (C2), 153.5 (C4), 135.0 (C8), 113.6 (C5), 37.8 (3×$CH_3$); m/z (FAB) 192 ($M^+$—Cl, 8%), 178 ($MH^+$—$CH_3Cl$, 72), 163 ($MH^+$—($CH_3$)$_2Cl$, 35), 149 ($MH_2^+$—($CH_3$)$_3Cl$, 100), 134 ($MH^+$—N($CH_3$)$_3Cl$, 45).

2-Amino-6-(1,4-diazabicyclo[2,2,2]oct-1-yl)purinium chloride ('DABCO-purine')

1,4-Diazabicyclo[2,2,2]octane (3.30 g, 29.3 mmol) was added to a solution of 2-amino-6-chloropurine (1.00 g, 5.9 mmol) in anhydrous DMSO (20 ml) under nitrogen. The reaction was stirred at room temperature for 12 h and the product collected by filtration under reduced pressure and dried in vacuo. Recrystallisation from isopropanol and water yielded the title compound as a white solid (1.49 g, 90%) (m.p. >230° C.) (Found C, 45.35; H, 5.9; N, 33.65 $C_{11}H_{16}N_7Cl+0.5$ M $H_2O$ requires C, 45.5; H, 5.9; N, 33.8%). $\nu_{max}/cm^{-1}$ 3450 ($NH_2$), 3300 (NH), 1640 (C=C), 1580 (C=N), 1250 (CO); $\lambda_{max}$ ($CH_3OH$)/nm 317; $\delta_H$ (200 MHz, $D_2O$) 8.21 (1H, s, C(8)H), 4.15 and 3.39(2×[6H, t, J=7], DABCO); $\delta_C$ (125.75 MHz, $D_2O$) 154.2 (C6), 152.0 (C2), 146.0 (C4), 138.9 (C8), 112.1 (C5), 48.7 and 39.5 (DABCO); m/z (+E.I) 281 ($M^+$, 6%), 245 ($M^+$—CL, 8), 189 (7), 163 (51), 113 (DABCO-$H^+$, 5). 36 (100).

6-Benzyloxypurine (NU2002)

Sodium (2.5 g, 109 mmol) was added to distilled benzyl alcohol (45 ml) under nitrogen. 6-Chloropurine (1.0 g, 6.47 mmol) was dissolved in distilled benzyl alcohol (73 ml) and the above solution (27 ml, 64.7 mmol) was added. The reaction was stirred at 100° C. under nitrogen for 5 days. After cooling to room temperature and neutralisation using glacial acetic acid, the solvent was removed in vacuo. Water (70 ml) was added and the product was extracted into ethyl acetate (3×30 ml). The combined organic extracts were dried over $MgSO_4$ and the solvent was removed. After further drying in vacuo, the product was recrystallised from acetone to yield the title compound as a white crystalline solid (0.39 g, 28%), m.p. 173–175° C.; (Found: C, 63.14; H, 4.29; N, 24.80. Calc. for $C_{12}H_{10}N_4O$: C, 63.71; H, 4.46; N, 24.76%); δH (200 MHz, $d_6$-DMSO) 8.480 (1H, s, C(2)H or C(8)H), 8.307 (1H, s, C(2)H or C(8)H), 7.522–7.301 (5H, m, Ph), 5.592 (2H, s, $OCH_2$); m/z 226 ($M^+$, 36%), 197 (8), 120 (35), 91 ($Bn^+$, 100%), 81 (9), 65 (24), 57 (23), 43 (16), 32 (8).

$O^6$-Methylguanine (NU2004)

Method A

Sodium (1.0 g, 44.2 mmol) was dissolved in methanol (30 ml) under nitrogen at room temperature. 2-Amino-6-chloropurine (1.5 g, 8.84 mmol) was added and the reaction refluxed under nitrogen for 48 h. After cooling the reaction was neutralised (glacial acetic acid), the solvents removed under reduced pressure and the residue recrystallised from water. The title compound was collected as a white crystalline solid (1.3 g, 89% )(m.p.>230° C.).

Method B

Anhydrous methanol (64 mg, 1.99 mmol) was added to sodium hydride (17 mg, 0.71 mmol) in anhydrous DMSO (0.4 ml). After 1 h 'DABCO-purine' (0.10 g, 0.36 mmol) was added and the reaction stirred for 12 h at room temperature. Acetic acid (0.06 ml) was added and the solvents removed in vacuo. The residue was purified by flash column chromatography on silica gel, eluting with 10% methanol in dichloromethane. The title compound was collected as a white solid (52 mg, 88%) (m.p.>230° C.). $\nu_{max}/cm^{-1}$ 3399 ($NH_2$), 3346 (NH), 3177 (CH), 2453 ($OCH_3$); $\lambda_{max}$ ($CH_3OH$)/nm 280; $\delta_H$ (200 MHz, $d_6$-DMSO) 7.92 (1H, s, C(8)H), 6.35 (2H, s, $NH_2$), 4.04 (3H, s, $OCH_3$); m/z (+EI) 165 ($M^+$, 100%), 134 ($M^+$—$OCH_3$, 20); $M^+$found 165.0643, $C_6H_7N_5O$ requires 165.0651.

$O^6$-Benzylguanine (NU2005)

Benzyl alcohol (215 mg, 1.99 mmol) was added to sodium hydride (0.017 g, 0.71 mmol) in anhydrous DMSO (0.4 ml). After 1 h 'DABCO-purine' (0.10 g, 0.36 mmol) was added and the reaction stirred for 48 h at room temperature. Acetic acid (0.06 ml) was added and the solvents removed in vacuo. The residue was purified by flash column chromatography on silica gel, eluting with 10% methanol in dichloromethane. The title compound was collected as a white solid (69 mg, 81%). $\lambda_{max}$ ($CH_3OH$)/nm 285; $\delta_H$ (200 MHz, $d_6$-DMSO) 7.96 (1H, s, C(8)H), 7.40 (5H, m, Ph), 6.44 (2H, s, $NH_2$), 5.61 (2H, s, $OCH_2$).

6-Allyloxypurine (NU2013)

Sodium (2.0 g, 86.96 mmol) was added to distilled allyl alcohol (35 ml) under nitrogen. 6-Chloropurine (1.0 g, 6.47 mmol) was dissolved in distilled allyl alcohol (35 ml) and the sodium allyloxide solution (33 ml) was added. The reaction was heated to 100° C. for 20 h, under nitrogen. After cooling, neutralisation of the reaction mixture, followed by recrystallisation of the residue from water, gave a white crystalline solid (550 mg, 48%), m.p. 199–200° C.; (Found: C, 54.35; H, 4.49; N. 32.06. Calc. for $C_8H_8N_4O$: C, 54.54; H, 4.58; N, 31.80%); $\nu_{max}$ ($cm^{-1}$) 3052, 2977, 2811 (NH, C—H) δH (200 MHz, $d_6$-DMSO) 8.526 (1H, s, C(2)H or C(8)H), 8.438 (1H, s, C(2)H or C(8)H). 6.280–6.086 (1H, dddd, CH=$CH_2$), 5.485 (1H, dd, $J_{gem}$=1.5Hz, $J_{trans}$=17.2 Hz, =$CH_2$), 5.325 (1H, dd, $J_{gem}$=1.5 Hz, $J_{cis}$=10.4 Hz, =$CH_2$), 5.107 (2H, d, J=5.5 Hz, $OCH_2$); m/z 176 ($M^+$, 43%), 174 ($M^+$, 43%), 161 (31), 147 (39), 136 ([MH—$CH_2CH=CH_2$]$^+$, 21%), 120 ([MH—$OCH_2CH=CH_2$]$^+$, 49%), 108 (13), 93 (37), 81 (11), 69 (32), 66 (18), 53 (26), 41 ([$CH_2CH=CH_2$]$^+$, 63%), 28 (62);

6-Cyclohexylmethoxypurine (NU2017)

Sodium (0.4 g, 17.4 mmol) was added to stirred cyclohexylmethanol (10 ml) under nitrogen. The reaction was stirred at 100° C. until no sodium remained. 6-Chloropurine (500 mg, 3.24 mmol) was added, and the reaction was stirred under nitrogen at 100° C. for 5 days. After cooling to room temperature, the mixture was neutralised with glacal acetic acid and the solvent was removed in vacuo. Water (20 ml) was added and the product was extracted into dichloromethane (3×30 ml). The combined organic extracts were dried over $MgSO_4$, and the volume of the solvent was doubled. After filtering hot and removal of the solvent, recrystallisation from ethyl acetate gave the title compound as a white crystalline solid (600 mg, 70%), m.p. 210–211° C.; (Found: C, 62.30; H, 6.93; N, 24.36. Calc. for $C_{12}H_{16}N_4O$: C, 62.05; H, 6.94; N, 24.12%); $v_{max}$ (cm$^{-1}$) 3108, 3050,2930, 2849, 2801 (NH, C—H); δH (200 MHz, d$_6$-DMSO) 8.479 (1H, s, C(2)H or C(8)H), 8.388 (1H, s, C(2)H or C(8)H), 4.348 (2H, d, J=6.2 Hz, OCH$_2$), 1.854–1.692 (6H, m, cyclohexyl), 1.357–0.984 (5H, m, cyclohexyl); δC (50 MHz, d$_6$-DMSO) 159.40, 155, 151.57, 142.88, 118, 71.41 (OCH$_2$), 37.08, 29.40, 26.24, 25.47 (cyclohexyl); m/z 233 (MH$^+$, 76%), 202 (33), 149 ([M—C$_6$H$_{11}$]$^+$, 32%), 137 (100), 120 ([MH—C$_7$H$_{13}$O]$^+$, 44%), 108 (30), 93 (27), 81 (65), 67 (62), 55 (88), 41 (89).

6-(2-Phenylethyloxy)purine (NU2023)

2-Phenylethanol (13 ml) was stirred under nitrogen and sodium (0.75 g, 32.36 mmol) was added. The reaction was heated to 60° C. When no sodium remained, anhydrous THF (18 ml) and 6-chloropurine (1.0 g, 6.47 mmol) were added. After refluxing under nitrogen for 5 h, the reaction mixture was allowed cool to room temperature and neutralised with glacial acetic acid. The THF was removed and the remaining alcohol was removed in vacuo. The product was recrystallised from ethanol and isolated as a white crystalline solid (962 mg, 62%), m.p. 209–210° C.; (Found: C, 64.57; H, 5.12; N, 23.54. Calc. for $C_{13}H_{12}N_4O$: C, 64.99; H, 5.03; N, 23.34%); $v_{max}$ (cm$^{-1}$) 3135,3063, 3031, 2948, 2897, 2797, 2672, 2583 (NH, C—H); δH (200 MHz, d$_6$-DMSO) 8.483 (1H, s, C(2)H or C(8)H), 8.365 (1H, s, C(2)H or C(8)H), 7.366–7.194 (5H, m, Ph), 4.741 (2H, t, J=7.0 Hz, OCH$_2$), 3.134 (2H, t, J=7.0 Hz, CH$_2$Ph); m/z 240 (M$^+$, 11%), 149 ([M—Bn]$^+$, 11%), 136 ([M—CH$_2$CH$_2$Ph]$^+$, 87%), 119 ([M—OCH$_2$CH$_2$Ph]$^+$, 40%), 104 ([CH$_2$CH$_2$Ph]$^+$, 100%), 91 (BN$^+$, 37%), 77 (Ph$^+$, 55%), 69 (48), 65 (15), 51 (26).

O$^6$-Allylguanine (NU2028)

Allyl alcohol (116 mg, 1.99 mmol) was added to sodium hydride (0.017 g, 0.007 mmol) in anhydrous DMSO (0.4 ml). After 1 h 'DABCO-purine' (0.10 g, 0.36 mmol) was added and the reaction stirred under nitrogen at room temperature. After 12 h acetic acid (0.06 ml) was added and the solvents removed in vacuo. The residue was purified by flash column chromatography on silica gel, eluting with 10% methanol in dichloromethane. The title compound was collected as a white solid (59 mg, 87%). $\lambda_{max}$ (CH$_3$OH)/nm 282; $\delta_H$ (200 MHz, d$_6$-DMSO) 8.42 (1H, s, C(8)H), 7.92 (2H, s, NH$_2$), 6.20 (1H, tdd, C(2')H), 5.51 (1H, d, J$_{trans}$ 17.2, C(3')H), 5.37 (1H, d, J$_{cis}$ 10.4, C(3')H, 5.03 (2H, d, J$_{vic}$ 5.5, CH$_2$O); m/z (+E.I) 191 (M$^+$, 47%), 165 (MH$^+$—CH=CH$_2$, 25), 135 (MH$^+$—OCH$_2$CH=CH$_2$, 25); M$^+$found 191.0814, C$_8$H$_9$N$_5$O requires 191.0807.

O$^6$-Propargylguanine (NU2031)

Propargyl alcohol (110 mg, 1.99 mmol) was added to sodium hydride (0.017 g, 0.007 mmol) in anhydrous DMSO (0.4 ml). After 1 h 'DABCO-purine' (0.10 g, 0.36 mmol) was added and the reaction stirred for 48 h at room temperature. Acetic acid (0.06 ml) was added and the solvents removed in vacuo. The residue was purified by flash column chromatography on silica gel, eluting with 10% methanol in dichloromethane. The title compound was collected as a white solid (48 mg, 72%). $\lambda_{max}$(CH$_3$OH)/nm 290; $\delta_H$ (200 MHz, d$_6$-DMSO) 8.42 (1H, s, C(8)H), 6.47 (2H, s, NH$_2$), 5.20 (2H, s, CH$_2$O),3.69 (1H, t, J=2.4, C(3')H).

O$^6$-(2-Oxo-2-phenylethyl)guanine (NU2033)

A—Preparation of O$^6$-(2,2-Dimethoxy-2-phenylethyl)guanine

Sodium hydride (231 mg, 9.6 mmol) was suspended in anhydrous THF (30 ml) and 2,2-dimethoxy-2-phenylethanol (680 mg, 3.74 mmol) in anhydrous THF (20 ml) was added dropwise. The reaction was stirred for 5 min and then 2-amino-6-chloropurine (317 mg, 1.87 mmol) was added. The reaction was refluxed overnight. The reaction mixture was neutralised with glacial acetic acid and the THF was removed. After dissolving the residue in methanol, silica was added. The solvent was removed and the product was purified by column chromatography using dichloromethane/ethanol (8.5:1.5) as eluent, and obtained as a white solid (420 mg, 71%). Further purification by recrystallisation from ethyl acetate afforded the title compound as a white solid, m.p. 208–209° C.; (Found: C, 57.43; H, 5.40; N, 22.14. Calc. for $C_{15}H_{17}N_5O_3$: C, 57.14; H, 5.43; N, 22.21%); $v_{max}$ (cm$^{-1}$) 3497,3438, 3310,3206,2946,2832, 1626 (NH, C—H, NH$_2$); δH (200 MHz, d$_6$-DMSO) 7.772 (1H, s, C(8)H), 7.571–7.530 (2H, m, Ph), 7.376–7.338 (314, m, Ph), 6.288 (2H, br s, NH$_2$), 4.682 (2H, s, CH$_2$), 3.180 (6H, s, OCH$_3$); m/z 315 (M$^+$, 42%), 284 ([M—OMe]$^+$, 48%), 252 (34), 165 ([M—CH$_2$C(OMe)$_2$Ph]$^+$, 80%), 151 ([CH$_2$C(OMe)$_2$Ph]$^+$, 79%), 134 (69), 105 ([PhCO]$^+$, 100%), 91 (BN$^+$, 55%), 59 (42), 43 (82).

B—Preparation of O$^6$-(2-Oxo-2-phenylethyl)guanine (NU2033)

O$^6$-(2,2-Dimethoxy-2-phenylethyl)guanine (90 mg, 0.29 mmol) was dissolved in aqueous acetic acid (3 M, 20 ml) and the reaction was stirred for 4 days. The solvent was removed in vacuo. The product was purified by dissolving in methanol followed by precipitation with ether. The title compound was obtained as a white solid (27 mg, 35%), m.p.>230° C.; (Found: C, 57.69; H, 4.20; N, 25.57. Calc. for $C_{13}H_{11}N_5O_2$: C, 57.99; H, 4.12; N, 26.01%); $v_{max}$ (cm$^{-1}$) 4390, 3391, 3061, 2973, 2924 (NH, C—H, NH$_2$), 1690 (C=O); $\lambda_{max}$(EtOH) 207 nm (ε 51,500), 241 nm (ε 28,200), 282 nm (ε 13,100); δH (200 MHz, d$_6$-DMSO) 8.041–7.998 (2H, m, Ph), 7.866 (1H, s, C(8)H), 7.707–7.545 (3H1 m, Ph), 6.178 (2H, br s, NH$_2$) 5.897 (2H, s, CH$_2$); m/z 270 ([MH]$^+$, 50%), 241 (38), 164 ([M—PhCO]$^+$, 51%), 134 (71). 105 ([PhCO]$^+$, 100%), 91 (BN$^+$, 65%), 77 (Ph$^+$, 82%), 65 (50), 53 (55), 43 (67).

O$^6$-(2-Methylallyl)guanine (NU2034)

To 2-methyl-2-propen-1-ol (10 ml) was added sodium (0.4 g, 17.4 mmol). The addition was carried out under nitrogen. When all of the sodium had reacted, 2-amino-6-chloropurine (500 mg, 2.95 mmol) and THF (10 ml) were added and the mixture was refluxed for 4 h. After cooling to room temperature, the reaction mixture was neutralised with glacial acetic acid and the solvent was removed. Water (20 ml) was added and the product was extracted into ethyl acetate (4×35 ml). The organic extracts were dried over MgSO$_4$ and the solvent was removed. Ethanol/dichloromethane (1:7) was added and the solution was triturated with ether. The precipitate that formed was collected by suction filtration and recrystallised from ethyl acetate to give the product as a white solid (363 mg, 60%), m.p. 176–178° C.; (Found 205.0967, C$_9$H$_{11}$N$_5$O requires 205.09722); $v_{max}$ (cm$^{-1}$) 3494, 3314, 3185, 2978, 2782 (NH, C—H, NH$_2$); δH (200 MHz, d$_6$-DMSO) 7.839 (1H, s, C(8)H), 6.275 (2H, s, NH$_2$), 5.057 (1H, s, =CH$_2$), 4.933 (1H, s, =CH$_2$), 4.855 (2H, s, OCH$_2$), 1.775 (3H, s, CH$_3$); m/z 205 (M$^+$, 42%), 188 (43), 176 (19), 135 ([MH—OCH$_2$C(CH$_3$)=CH$_2$]$^+$, 20%), 108 (15), 81 (14), 69 (35), 55 ([OCH$_2$C(CH$_3$)=CH$_2$]$^+$, 46%), 41 (35), 32 (100).

O$^6$-(2-Oxopropyl)guanine (NU2035)

O$^6$-(2,2-Diethoxypropyl)guanine (500 mg, 1.78 mmol) was suspended in aqueous acetic acid (1 M, 12 ml) and the suspension was stirred for 2 days at room temperature. After this time, all of the solid had dissolved and the solvent was removed in vacuo. The residue was recrystallised from acetone yielding the required product as a white solid (183 mg, 50%), m.p. 195–196° C.; $v_{max}$ (cm$^{-1}$) 3355,3119, 2780 (NH, NH$_2$, C—H), 1734 (C=O); δH (200 MHz, d$_6$-DMSO) 7.902 (1H, s, C(8)H), 6.270 (2H, s, NH$_2$), 5.069 (2H, s, OCH$_2$), 2.175 (3H, s, COCH$_3$); nm/z 207 (M$^+$, 53%), 192 ([M—CH$_3$]$^+$, 15%), 164 ([M—COCH$_3$]$^+$, 45%), 134 ([M—OCH$_2$COCH$_3$]$^+$, 73%), 119 (10), 108 (23), 92 (12), 80 (11), 65 (12), 53 (25), 43 ([COCH$_3$]$^+$, 85%), 32 (100).

N$^9$,O$^6$-Diallylguanine (NU2036)

Sodium (0.3 g, 12.65 mmol) was reacted with allyl alcohol (12 ml) and N$^9$-allyl-2-amino-6-chloropurine (530 mg, 2.53 nimol) was added. The reaction was refluxed for 30 min, after which time the mixture was cooled and neutralised with glacial acetic acid. The solvent was removed and water (30 ml) was added. The product was extracted into ethyl acetate (3×40 ml) and the organic extracts were dried over Na$_2$SO$_4$. After removal of the solvent, the product was purified by column chromatography on silica using ethyl acetate as the eluting solvent. The title compound was obtained as a white crystalline solid (500 mg, 86%) and further purified by recrystallisation from ethyl acetate/petrol, m.p. 86–87° C.; (Found: C, 57.36; H, 5.75; N, 29.50. Calc. for C$_{11}$H$_{13}$N$_5$O: C, 57.13; H, 5.67; N, 30.28%); $v_{max}$ (cm$^{-1}$) 3397,3333, 3220,3092, 2940 (NH$_2$, C—H); δH (200 Mz, d$_6$-DMSO) 7.844 (1H, s, C(8)H), 6.446 (2H, s, NH$_2$), 6.216–5.939 (2H, m, NCH$_2$CH=CH$_2$ and OCH$_2$CH=CH$_2$), 5.476–4.900 (4H, series of dd, NCH$_2$CH=CH$_2$ and OCH$_2$CH=CH$_2$), 4.948 (2H, m, OCH$_2$CH=CH$_2$), 4.656 (2H, m, NCH$_2$CH=CH$_2$); δC (50 MHz, d$_6$-DMSO) 160.26, 160.13, 154.58, 140.05, 133.81, 133.68, 118.34, 117.21, 113.90, 66.34 (OCH$_2$), 44.92 (NCH$_2$); m/z 231 (M$^+$, 80%), 202 (22), 190 ([M—CH$_2$CH=CH$_2$]$^+$, 14%), 175 (20), 121 (21), 91 (23), 83 (40), 73 (60), 69, (79),55 (100).

N$^7$,O$^6$-Diallylguanine (NU2037)

Sodium (120 mg, 5.25 mmol) was reacted with allyl alcohol (5 ml) and N$^7$-allyl-2-amino-6-chloropurine (220 mg, 1.05 mmol) was added. The reaction was refluxed for 30 min, after which time the mixture was cooled and neutralised with glacial acetic acid. The solvent was removed and water (30 ml) was added. The product was extracted into ethyl acetate (3×40 ml) and the organic extracts dried over Na$_2$SO$_4$. The solvent was removed and the product was purified by column chromatography on silica using ethyl acetate as the eluting solvent. The title compound was obtained as a white crystalline solid (175 mg, 72%), and was further purified by recrystallisation from ethyl acetate/petrol, m.p. 105–107° C.; $v_{max}$ (cm$^{-1}$) 3387, 3314, 3198, 3090, 3015, 2990, 2934, 2379 (NH$_2$, C—H); δH (200 MHz, d$_6$-DMSO) 8.089 (1H, s, C(8)H), 6.153 (2H, s, NH$_2$), 6.187-5.979 (2H, m, NCH$_2$CH=CH$_2$ and OCH$_2$CH=CH$_2$), 5.406 (1H, dd, J$_{gem}$=1.6 Hz, J$_{trans}$=17.3 Hz, OCH$_2$CH=CH$_2$), 5.270 (1H, dd, Jgem=1.6 Hz, J$_{cis}$=10.5 Hz, OCH$_2$CH=CH$_2$), 5.169 (1H, dd, J$_{gem}$=1.3 Hz, J$_{cis}$=10.3 Hz, NCH$_2$CH=CH?), 4.978 (1H, dd, J$_{gem}$=1.3 Hz, NCH$_2$CH=CH$_2$), 4.921 (2H, d, J=5.3 Hz, OCH$_2$CH=CH$_2$), 4.826 (2H, d, J=5.3 Hz, NCH$_2$CH=CH$_2$); m/z 231 (M$^+$, 62%), 216 ([MH—NH$_2$]$^+$, 13%), 190 ([M—CH$_2$CH=CH$_2$]$^+$, 10%), 173 (MH—OCH$_2$CH=CH$_2$]$^+$, 7%), 151 (7), 122 (8), 91 (19), 83 (9), 68 (14), 60 (100).

O$^6$-Allyl-N$^9$-benzylguanine (NU2038)

Allyl alcohol (15 ml) was cooled to 0° C. and sodium (0.18 g, 7.7 mmol) was added. The solution was allowed to reach room temperature and 2-amino-N$^9$-benzyl-6-chloropurine (400 mg, 1.54 mmol) was added. The reaction mixture was refluxed under nitrogen for 1¾ h. The reaction mixture was allowed to cool to room temperature and neutralised with glacial acetic acid. Water (20 ml) was added and the product was extracted into ethyl acetate (3×35 ml). The organic extracts were combined and dried over MgSO$_4$. The solvent was removed and the residue was recrystallised from petrol/ethyl acetate to give the title compound as a white crystalline solid (300 mg, 69%), m.p. 113–114° C.; (Found: C, 63.66; H, 5.16; N, 24.72. Calc. for C$_{15}$H$_{15}$N$_5$O: C, 64.04; H, 5.37; N, 24.90%); $v_{max}$ (cm$^{-1}$) 3499, 3320, 3195, 3087, 3058,3023 (NH$_2$, C—H); δH (200 MHz, d$_6$-DMSO) 7.967 (1H, s, C(8)H), 7.382–7.199 (5H, m, Ph), 6.460 (2H, s, NH$_2$), 6.181–6.015 (1H, m, CH=CH$_2$), 5.415 (1H, dd, J$_{trans}$=17.2 Hz, J$_{gem}$=1.7 Hz, CH=CH$_2$), 5.276 (1H, dd, CH=CH$_2$), 5.253 (2H, s, CH$_2$Ph), 4.945 (2H, d, J=5.6 Hz, OCH$_2$); δC (50 MHz, d$_6$-DMSO) 160.31, 160.21, 154.72, 140.21, 137.57, 133.67, 128.97, 127.89, 127.38, 118.35, 113.97, 66.35, 46.09; m/z 281 (M$^+$, 61%), 252 (12), 225 ([MH—OCH$_2$CH=CH$_2$]$^+$, 9%), 190 ([M—Bn]$^+$, 44%), 135 ([MH—OCH$_2$CH=CH$_2$—Bn]$^+$, 10%), 91 (BN$^+$, 100%), 65 (29), 41 ([CH$_2$CH=CH$_2$]$^+$, 34%), 32 (72).

O$^6$-(2-Phenylethyl)guanine (NU2041)

Sodium hydride (265 mg, 11 mmol) was suspended in anhydrous THF (40 ml) and 2-phenylethanol (3 ml) in THF (7 ml) was added with cooling. The reaction was stirred for 1 h and allowed to reach room temperature. 2-Amino-6-chloropurine (750 mg, 4.42 mmol) was added, and the reaction was refluxed for 1 h and then stirred at room temperature overnight. The reaction mixture was neutralised with glacial acetic acid and the solvent was removed. After purification by chromatography on silica using 15% ethanol in dichloromethane as eluent, followed by recrystallisation from ethyl acetate, the product was obtained as a white solid (549 mg, 49%), m.p. 206–207° C.; (Found: C, 61.32; H, 5.06; N. 26.64. Calc. for C$_{13}$H$_{13}$N$_5$O: C, 61.17; H, 5.13; N, 27.43%); $v_{max}$ (cm$^{-1}$) 3495, 3366,3127, 2982, 2801 (NH, NH$_2$, C—H); δH (200 MHz, d$_6$-DMSO) 7.803 (1H, s, C(8)H), 7.371–7.221 (SH, m, Ph), 6.271 (2H, s, NH$_2$), 4.584 (2H, t, J=7.2 Hz, OCH$_2$), 3.084 (2H, t, J=7.2 Hz, CH$_2$Ph); m/z 255 (M$^+$, 26%), 151 ([MH—CH$_2$CH$_2$Ph]$^+$, 100%), 134 ([M—OCH$_2$CH$_2$Ph]$^+$, 24%), 105 (CH$_2$CH$_2$Ph]$^+$, 41%), 97 (38), 91 (BN$^+$, 23%), 81 (51), 69 (86), 55 (82).

O$^6$-(2-Phenylallyl)guanine (NU2042)

Sodium hydride (450 mg, 7.9 mmol) was suspended in anhydrous THF (30 ml) under nitrogen. 3-Hydroxy-2-phenyl-1-propene (820 mg, 6.12 mmol) in anhydrous THF (20 ml) was added slowly and the reaction mixture was stirred for 15 min. 2-Amino-6-chloropurine (700 mg, 4.13 mmol) was added, and the mixture was refluxed for 12 h. After cooling to room temperature, and neutralised with glacial acetic acid, the solvent was removed. The residue was stirred in hot methanol and filtered, followed by the addition of silica and removal of the solvent. The product was isolated by column chromatography on silica using dichloromethane/ethanol (9:1) as eluent. The product was recrystallised from ethyl acetate and obtained as a white solid (206 mg, 19%), m.p.83–85° C.; $v_{max}$ (cm$^{-1}$) 3484, 3326,3189, 2787, 1622, 1586 (NH, C—H, NH$_2$); $\lambda_{max}$ (EtOH) 205 nm (ε 84,570), 228 nm (ε 32,450), 283 nm (ε

14,000); δH (200 MHz, d$_4$-methanol) 8.023 (1H, s, C(8)H), 7.750–7.565 (2H, m, Ph), 7.536–7.464 (3H, m, Ph), 5.817 (1H, s, =CH$_2$), 5.731 (1H, s, =CH$_2$), 5.652 (2H, s, OCH$_2$); m/z 267 (M$^+$, 80%), 250 (68), 151 ([MH—CH$_2$C(Ph)=CH$_2$]$^+$, 41%), 134 ([M—OCH$_2$C(Ph)=CH$_2$]$^+$, 47%), 115 (100), 91 (BN$^+$, 76%), 77 (Ph$^+$, 25%), 69 (43), 44 (50).

O$^{6\text{-}n}$Propylguanine (NU2045)

Sodium (0.35 g, 15.2 mmol) was added to anhydrous n-propanol (30 ml) under nitrogen. When all of the sodium had reacted 2-amino-6-chloropurine (500 mg, 2.95 mmol) was added. The reaction was refluxed for 24 h. After cooling the reaction mixture was neutralised with glacial acetic acid and the solvent was removed. The product was recrystallised from water to give the title compound as a white solid (204 mg, 36%), m.p. 199–201° C.; (M$^+$Found 193.0938, C$_8$H$_{11}$N$_5$O requires 193.09124); ν$_{max}$ (cm$^{-1}$) 3490,3301, 3173, 2975, 2886, 2780, 2539 (NH, C—H, NH$_2$); δH (200 MHz, d$_6$-DMSO) 7.795 (1H, s, C(8)H), 6.222 (2H, s, NH$_2$), 4.333 (2H, t, J=7 Hz, OCH$_2$), 1.759 (2H, sextet, J=7 Hz, CH$_2$CH$_2$CH$_3$), 0.968 (3H, t, J=7 Hz, CH$_3$); m/z 193 (M$^+$, 37%), 164 ([M—Et]$^+$, 8%), 151 ([M—Pr]$^+$, 56%), 143 (4), 134 ([M—OPr]$^+$, 25%), 109 (20), 69 (100), 51 (9), 43 (Pr+, 10%), 32 (23).

O$^6$-Ethylguanine (NU2046)

Sodium (0.5 g, 22 mmol) was added to anhydrous ethanol (50 ml) under nitrogen. When all of the sodium had reacted, 2-amino-6-chloropurine (750 mg, 4.42 mmol) was added. The reaction was refluxed for 3 h. After cooling, the reaction mixture was neutralised with glacial acetic acid and the solvent was removed. Recrystallisation from water gave the product as a white solid (548 mg, 69%), m.p.>230° C.; (Found: C, 46.76; H, 4.97; N, 39.09. Calc. for C$_7$H$_9$N$_5$O: C, 46.92; H, 5.06; N, 39.09%); ν$_{max}$ (cm$^{-1}$) 3505, 3484, 3432, 3324, 3191, 3110, 2984, 2901, 2705, 2544 (NH, C—H, NH$_2$); δH (200 MHz, d$_6$-DMSO) 7.808 (1H, s, C(8)H), 6.224 (2H, s, NH$_2$), 4.437 (2H, q, J=7.1 Hz, OCH$_2$), 1.353 (3H, t, J=7.1 Hz. CH$_2$CH$_3$); m/z 179 (M$^+$, 100%), 169 (19), 164 (35), 151 ([MH—Et]$^+$, 36%), 135 ([MH—OEt]$^+$, 43%), 131 (38), 119 (34), 109 (54), 81 (41), 69 (39), 60 (21), 55 (31), 41 (48),

O$^6$-Allyl-N$^2$-dimethylguanine (NU2048)

6-Allyloxy-2-chloropurine (50 mg, 0.24 mmol) was dissolved in DMF (1 ml) and distilled ethanolamine (50 μl, 0.83 mmol) was added. The reaction was heated at 90° C. for 3 days. The solvent was removed and the residue was purified by chromatography on silica using 8% ethanol in dichloromethane as the eluting solvent. The title compound was obtained as a white solid (36 mg, 68%), which was further purified by recrystallisation from ethyl acetate, m.p. 176–177° C.; (Found: C, 55.12; H, 5.94; N, 31.88. Calc. for C$_{10}$H$_{13}$N$_5$O: C, 54.78; H, 5.98; N, 31.94%); ν$_{max}$ (cm$^{-1}$) 3100, 2938,2865 (NH, C—H); δH (200 MHz, d$_6$-DMSO) 7.883 (1H, s, C(8)H), 6.219–6.025 (1H, m, CH$_2$CH=CH$_2$), 5.419 (1H, m, CH$_2$CH=CH$_2$), 5.270 (1H, m, CH$_2$CH=CH$_2$), 4.978 (2H, d. J=5.6 Hz, CH$_2$CH=CH$_2$), 3.098 (6H, s, NMe$_2$); m/z 219 (M$^+$, 83%), 204 ([M—Me]$^+$, 45%), 190 ([M-2Me]$^+$, 58%), 178 ([M—CH$_2$CH=CH$_2$]$^+$, 77%), 164 (29), 149 (43), 135 ([M—NMe$_2$-CH$_2$CH=CH$_2$]$^+$, 91%), 71 (24), 53 (28),41 ([CH$_2$CH=CH$_2$]$^+$, 100%), 28 (97).

6-Allyloxy-2-chloropurine (NU2051)

Sodium (0.37 g, 15.9 mmol) was reacted with allyl alcohol (20 ml) under nitrogen with cooling in an ice bath. 2,6-Dichloropurine (1.00 g, 5.29 mmol) was added and the reaction was refluxed for 2 h, after which time the reaction mixture was allowed to cool. The mixture was neutralised with glacial acetic acid and the solvent was removed. The residue was triturated with cold water to yield the title compound as a white solid (1.05 g, 94%), m.p. 208–209° C.; ν$_{max}$ (cm$^{-1}$) 3422,3017, 2782, 2685, 2595 (NH, C—H); δH (200 MHz, d$_6$-DMSO) 8.454 (1H, s, C(8)H), 6.230–6.036 (1H, m, CH$_2$CH=CH$_2$), 5.478 (1H, dd, J=1.6 Hz, J=17.2 Hz, CH$_2$CH=CH$_2$), 5.327 (1H, dd, J=1.6 Hz, J=10.4 Hz, CN$_2$CH=CH$_2$), 5.054 (2H, d, J=5.5 Hz, CH$_2$CH=CH$_2$); m/z 210 (M$^+$, 68%), 195 (64), 183 (12), 175 ([M—Cl]$^+$, 98%), 154 ([MH—OCH$_2$CH=CH$_2$]$^+$, 21%), 135 ([MH—Cl—CH$_2$CH=CH$_2$]$^+$, 50%), 119 ([MH—Cl—OCH$_2$CH=CH$_2$]$^+$, 33%), 92 (12), 53 (18), 41 ([CH$_2$CH=CH$_2$]$^+$, 100%), 32 (53).

O$^{6\text{-}n}$Butylguanine (NU2052)

Sodium (0.34 g, 15 mmol) was added to anhydrous n-butanol (20 ml) under nitrogen. When all of the sodium had reacted 2-amino-6-chloropurine (500 mg, 2.95 mmol) was added. The reaction was heated at 70° C. overnight. After cooling the reaction mixture was neutralised with glacial acetic acid. The solvent was removed and the product was recrystallised from water to give the title compound as a white solid (331 mg, 54%), m.p. 176–178° C. (Found: C, 52.38; H, 6.56; N, 33.59. Calc. for C$_9$H$_{13}$N$_5$O: C, 52.16; H, 6.32; N, 33.79%); ν$_{max}$ (cm$^{-1}$) 3501, 3374, 3106, 2955, 2874, 2803 (NH, C—H, NH$_2$); δH (200 MNHz, d$_6$-DMSO) 7.798 (1H, s, C(8)H), 6.219 (2H, br s, NH$_2$), 4.381 (2H, t, J=6.7 Hz, OCH$_2$), 1.731 (2H, m, CH$_2$CH$_2$CH$_2$), 1.420 (2H, m, CH$_2$CH$_3$), 0.934 (3H, t, J=7.2 Hz, CH$_3$); mz 207 (M$^+$, 72%), 164 ([M-$^n$Pr]$^+$, 10%), 151 ([MH-$^n$Bu]$^+$, 100%), 134 ([M—O$^n$Bu]$^+$, 55%), 122 (10), 109 (50), 80 (8), 54 (15), 43 (25), 28 (7).

O$^6$-(3'-Methyl)butylguanine (NU2053)

Sodium (1.0 g, 44.2 mmol) was dissolved in 3-methyl-1-butanol (60 ml) under nitrogen. 2-Amino-6-chloropurine (1.5 g, 8.84 mmol) was added and the reaction stirred at reflux for 48 h under nitrogen . The reaction was neutralised (glacial acetic acid), the solvent removed in vacuo and the residue recrystallised from water to afford the title compound as a white crystalline solid (1.09 g, 56% )(m.p.175° C.). (Found C, 54.35; H, 6.7; N, 31.5 C$_{10}$H$_{15}$N$_5$O requires C, 54.3; H, 6.8; N, 31.7%). ν$_{max}$/cm$^{-1}$ 3505 (NH$_2$), 3310 (NH), 3182 (CH), 2552 (CH$_2$); δ$_H$ (200 MHz, d$_6$-DMSO) 12.50 (1H, br s, NH), 7.92 (1H, s, C(8)H), 6.33 (2H, s, NH$_2$), 4.53 (2H, t, J=6.6, OCH$_2$), 1.89 (1H, m, CH(CH$_3$)$_2$), 1.78 (2H, m, OCH$_2$CH$_2$), 1.06 (6H, d, J 6.3, 2×CH$_3$); m/z (+EI) 221(M$^+$, 29%), 165 (MH$^+$—CH$_2$CH(CH$_3$)$_2$, 10), 151 (MH$^+$—(CH$_2$)$_2$CH(CH$_3$)$_2$, 88), 134 (M$^+$—O(CH$_2$)$_2$CH(CH$_3$)$_2$, 18).

O$^6$-(2-Ethylallyl)guanine (NU2054)

Sodium hydride (600 mg, 25 mmol) was suspended in anhydrous THF (40 ml) and 2-ethylallyl alcohol (1.0 g, 11.6 mmol) in THF (10 ml) was added. The reaction was stirred at room temperature for 30 min and 2-amino-6-chloropurine (1.0 g, 5.90 mmol) was added. The reaction was complete after 24 h at reflux, after which time the reaction mixture was allowed to cool and was neutralised with glacial acetic acid. Ethanol (40 ml) was added, followed by silica. The solvent was removed and the residual solid was added to the top of a silica column. Elution with 10% ethanol in dichloromethane yielded the title compound as a white solid after recrystallisation from ethyl acetate (650 mg. 50%), m.p. 148–149° C.; (Found 219.1121, $C_{10}H_{13}N_5O$ requires 219.11216); $v_{max}$ (cm$^{-1}$) 3465, 3306, 3200, 3137, 2965, 2940, 2915, 2882, 2803, 1630, 1584 (NH, C—H, NH$_2$); δH (200 MHz, d$_6$-DMSO) 7.833 (1H, s, C(8)H), 6.259 (2H, br s, NH$_2$), 5.124 (1H, s, =CH$_2$), 4.964 (1H, s, =CH$_2$). 4.915 (2H, s, OCH$_2$), 2.132 (2H, q, J=7.4 Hz, CH$_2$CH$_3$), 1.061 (3H, t, J=7.4 Hz, CH$_2$CH$_3$); δC (50 MHz, d$_6$-DMSO) 160, 159.99, 155.50, 146.48, 138.12, 113.83, 110.89, 67.77 (OCH$_2$), 25.79 (CH$_2$CH$_3$), 12.13 (CH$_3$); m/z 219 (M$^+$, 84%), 202 (86), 190 ([M—Et]$^+$, 90%), 176 (9), 164 ([M—C(Et)=CH$_2$]$^+$, 22%), 151 ([MH—CH$_2$C(Et)=CH$_2$]$^+$, 86%), 135 ([MH—OCH$_2$C(Et)=CH$_2$]$^+$, 90%), 109 (60), 69 ([CH$_2$C(Et)=CH$_2$]$^+$, 50%), 53 (52), 41 (100), 32 (30), 29 (54).

O$^6$-(2-Isopropylallyl)guanine (NU2055)

Sodium hydride (600 mg, 25 mmol) was suspended in anhydrous THF (40 ml) and 2-isopropylallyl alcohol (1.77 g, 17.7 mmol) in THF (10 ml) was added. The reaction was stirred at room temperature for 30 min and 2-amino-6-chloropurine (1.0 g, 5.90 mmol) was added. The reaction was complete after 24 h at reflux, after which time the reaction mixture was allowed to cool and was neutralised with glacial acetic acid. Ethanol (40 ml) was added, followed by silica. The solvent was removed and the product was purified by column chromatography using 10% ethanol in dichloromethane as eluent to give the title compound as a white solid after recrystallisation from ethyl acetate/petrol (470 mg, 34%), m.p. 170–172° C.; (Found 233.1268, $C_{11}H_{15}N_5O$ requires 233.12596);

$v_{max}$ (cm$^{-1}$) 3322,3189, 2963, 2872, 2789 (NH, C—H, NH$_2$); δH (200 MHz, d$_6$-DMSO) 7.808 (1H, s, C(8)H), 6.257 (2H, br s, NH$_2$), 5.098 (1H, d, J=1 Hz, =CH$_2$), 4.972 (1H, d, J=1 Hz, =CH$_2$), 4.953 (2H, s, OCH$_2$), 2.387 (1H, septet, J=6.8 Hz, CH(CH$_3$)$_2$), 1.074 (6H, d, J=6.8 Hz, CH(CH$_3$)$_2$); m/z 233 (M$^+$, 60%), 190 ([M-$^i$Pr]$^+$, 68%), 151 ([M—CH$_2$C($^i$Pr)=CH$_2$]$^+$, 95%), 108 (55), 91 (100), 79 (27), 70 (79), 55 (47), 41 (58).

O$^6$-(3-Methyl-2-oxobutyl)guanine. TFA (NU2056)

O$^6$-(3-Methyl-2-oxobutyl)guanine ethylene acetal (200 mg, 0.72 mmol) was dissolved in 80% aqueous trifluoroacetic acid (10 ml) and the reaction was stirred at room temperature for 4 days. After removal of the solvent in vacUo, the residue was recrystallised from ethanol. The title compound was obtained as a white salt (173 mg, 69%), m.p. (decomposed);

(Found 235.1063, $C_{1013}N_5O_2$ requires 235.10571); $v_{max}$ (cm$^{-1}$) 3854,3501, 3320.3183, 2977, 2940, 2791 (NH, NH$_2$, C—H), 1732 (C=O); δH (200 MHz, d$_6$-DMSO) 8.232 (1H, s, C(8)H), 6.624 (2H, s, NH), 5.261 (2H, s, OCH$_2$), 2.802 (1H, septet, J=6.9 Hz, CH(CH$_3$)$_2$), 1.092 (6H, d, J=6.9 Hz, CH(CH$_3$)$_2$); m/z 235 (M$^+$, 67%), 192 ([M-$^i$Pr]$^+$, 49%), 165 ([MH—COCH(CH$_3$)$_2$]$^+$, 60%), 135 ([MH—OR]$^+$, 75%), 108 (55), 91 (100), 69 (48), 55 (60), 43 (98), 28 (36).

O$^6$-(3-Methyl-2-oxobutyl)guanine ethylene acetal (NU2057)

Sodium hydride (264 mg, 11 mmol) was suspended in anhydrous THF (30 ml) and cooled in an ice bath. After the dropwise addition of 3-methyl-2-oxo-1-butanol ethylene acetal (946 mg, 6.48 mmol), the reaction was stirred under nitrogen for 15 min at room temperature. 2-Amino-6-chloropurine (733 mg, 4.32 mmol) was added and the reaction was refluxed for 8 h. After cooling to room temperature, the mixture was neutralised with glacial acetic acid and the solvent was removed. The residue was dissolved in methanol and silica was added. The solvent was removed to give a free-flowing solid. After loading onto a silica column, the product was purified by column chromatography using 10% ethanol in dichloromethane as the eluting solvent. The product was obtained as a white solid (620 mg, 51%), and was further purified by recrystallisation from ethyl acetate, m.p. 234–235° C.; (Found: C, 51.58; H, 5.84; N, 24.79. Calc. for $C_{12}H_{17}N_5O_3$: C, 51.61; H, 6.13; N, 25.02%); $v_{max}$ (cm$^{-1}$) 3459, 3343, 3223, 3133, 2980, 2878, 2799 (NH, NH?, C—H); δH (200 MHz, d$_6$-DMSO) 7.831 (1H, s, C(8)H), 6.274 (2H, s, NH$_2$), 4.418 (2H, s, OCH$_2$), 4.087–3.862 (4H, m, OCH$_2$CH$_2$O), 2.111 (1H, septet, J=6.9 Hz, CH(CH$_3$)2), 0.936 (611, d, J=6.9 Hz, CH(CH$_3$)$_2$); m/z 279 (M$^+$, 30%). 274 (5), 250 (46), 236 ([M-$^i$Pr]$^+$, 45%), 222 (13), 212 (42), 194 (5), 180 (5), 164 ([M—C(OCH2CH$_2$O)$^i$Pr)]$^+$, 52%), 152 (30), 134 ([M—OR]$^+$, 70%), 123 (35), 115 [(C(OCH$_2$CH$_2$O)$^i$Pr]$^+$, 100%), 96 (32), 82 (45), 67 (35), 55 (35), 43 ($^i$Pr+, 58%), 29 (16).

O$^6$-Cyclohexylmethylguanine (NU2058)

Cyclohexylmethanol (1.23 ml, 9.84 mmol) was added to anhydrous DMSO (8 ml) with sodium hydride (0.085 g, 3.54 mmol). After stirring under N$_2$ for 1 h, 2-amino-1,4-diazabicyclo[2,2,2]-octylpurin-6-ylammonium chloride (500 mg, 1.78 mmol) was added and the reaction mixture was left stirring at room temperature for 48 h. The resulting mixture was neutralised with glacial acetic acid (0.2 ml). DMSO and acetic acid were then removed and the crude product was columned on silica gel eluting with 10% methanol in dichloromethane, the product was isolated as a white solid (0.221 g, 51%); (Found: C, 50.88; H, 5.93; N, 24.29% $C_{12}H_{17}N_5O$ and 2 M H$_2$O requires C, 50.88; H, 6.0; N, 24.73%); $u_{max}$/cm$^{-1}$ 3350 (NH$_2$), 3200 (NH), 2900 (CH$_2$), 1640 (C=C); dH NMR (200 MHz, d$_6$-DMSO) 1.50 (11H, m, C(3')H, C(4')H, C(5')H and C(2')H, C(1')H, C(6') H), 4.29 (2H, d, J=6 Hz, OCH$_2$), 6.31 (2H, s, NH$_2$), 7.92 (1H, s, C(8)H); m/z (FAB) 247 (M$^+$, 14%), 151 (MH$^+$—C$_6$H$_{11}$CH$_2$, 100), 134 (M$^+$—OCH$_2$C$_6$H$_{11}$, 8), 81 (8).

O$^6$-(5'-Hexenyl)guanine (NU2061)

5-Hexen-1-ol (4 ml) was slowly added to a solution of sodium hydride (0.345 g, 14.7 mmol) in anhydrous THF (20 ml). 2-Amino-6-chloropurine (0.50 g, 2.95 mmol) was added after 30 min, and the reaction refluxed under nitrogen for 12 h. The reaction was cooled, neutralised (glacial acetic acid), the solvents removed and the residue recrystallised from water. The title compound was collected as a white solid (0.45 g, 70%)(m.p.203° C.). (Found C, 56.2; H, 6.3; N, 29.6 $C_{11}H_{15}N_5O$ requires C, 56.6; H, 6.5; N, 30.0%). $v_{max}$/cm$^{-1}$ 3483 (NH$_2$), 3302 (NH), 3181 (CH); δ$_H$ (200 MHz, d$_6$-DMSO) 12.50 (1H, br s, NH), 7.93 (1H, s, C(8)H), 6.33 (2H, s, NH$_2$), 5.94 (1H, m, CH$_2$=CH), 5.1 (2H, m, CH$_2$=CH), 4.49 (2H, t, J6.55, OCH$_2$), 2.22 (2H, q, CH$_2$CH), 1.87 (2H, m, OCH$_2$CH$_2$), 1.60 (2H, m, O(CH$_2$)$_2$CH$_2$CH$_2$CH=CH$_2$); δ$_C$ (50.3 MHz, d$_6$-DMSO) 160.1, 138.9, 115.3, 65.6, 33.2, 28.3, 25.1; m/z (+EI) 233 (M$^+$, 24%), 151 (MH$^+$—(CH$_2$)$_4$CH=CH$_2$, 100).

O$^6$-Heptylguanine (NU2064)

Sodium (0.5 g, 22.1 mmol) was dissolved in heptan-1-ol (20 ml) under nitrogen. After 30 min, 2-amino-6-chloropurine (0.75 g, 4.42 mmol) was added and the reaction refluxed under nitrogen for 36 h. After cooling, the reaction was neutralised (glacial acetic acid), the solvent removed and the residue recrystallised from water. The title compound was collected as a white solid (0.59 g, 54%)(m.p. 172–175° C.). (Found C, 57.8; H, 7.6; N, 27.7 $C_{12}H_{19}N_5O$ requires C, 57.8; H, 7.7; N, 28.1%). $v_{max}/cm^{-1}$ 3499 ($NH_2$), 3300 (NH), 3179 (CH); $\delta_H$ (200 MHz, $d_6$-DMSO) 12.50 (1H, br s, NH), 7.89 (1H, s, C(8)H), 6.33 (2H, s, $NH_2$), 4.47 (2H, t, J=6.6, $OCH_2$), 1.84 (2H, m, $OCH_2CH_2$), 1,38 (8H, m, $(CH_2)_4CH_3$), 0.96 (3H, t, J 6.4, $CH_3$); m/z (+EI) 249 ($M^+$, 52%), 164 ($M^+$—$(CH_2)_5CH_3$, 17), 151 ($MH^+$—$(CH_2)_6CH_3$, 10).

Synthesis of $O^6$-(trans-3'-Hexenyl)guanine (NU2067)

Sodium hydride (0.345 g, 14.74 mmol) was suspended in dry THF (20 ml) and trans-3-hexen-1-ol (2 ml, 16.3 mmol) was slowly added. After 30 min, 2-amino-6-chloropurine (0.50g, 2.95mmol) was added and the reaction refluxed under nitrogen for 24 h. The reaction was cooled, neutralised (glacial acetic acid), the solvents removed and the residue recrystallised from water. The title compound was collected as a white solid (0.42 g, 61%) (m.p. 204–205° C.) $v_{max}/cm^{-1}$ 3500 ($N_{12}$), 3190 (H), 3005 (CH); $\delta_H$ (200 MHz, $d_6$-DMSO) 12.50 (1H, s, NH), 7.91 (1H, s, C(8)H), 6.35 (2H, s, $NH_2$), 5.7–5.4 (2H, m, CH=CH) 2.6–2.5 (m, $CH_2CHCH$) 2.09 (2H, p, J 6.9, $CH_2CH_3$) 1.03 (3H, t, J 6.4, $CH_3$); m/z (+EI) 233 ($M^+$, 24%), 218 ($M^+$—$CH_3$, 2), 191 ($M^+$—$CHCH_2CH_3$, 165 ($MH^+$—$CH_2CHCHCH_2CH_3$, 9), 151 ($MH^+$—$(CH_2)_2CHCHCH_2CH_3$, 100), 134 ($MH^+$—$OCH_2CH_2CHCHCH_2CH_3$, 20).

$O^6$-(Cyclopentyl)methylguanine (NU2068)— Method A

Cyclopentane methanol (199 mg, 1.99 mmol) was added to sodium hydride (0.017 g, 0.007 mmol) in anhydrous DMSO (0.4 ml). After 1 h 'DABCO-purine' (0.10 g, 0.36 mmol) was added and the reaction stirred for 48 h at room temperature. Acetic acid (0.06 ml) was added and the solvents removed in vacuo. The residue was purified by flash column chromatography on silica gel, eluting with 10% methanol in dichloromethane. The title compound was collected as a white solid (67 mg, 82%) (m.p. 121° C.). (Found: C, 54.4; H, 6.5; N, 28.5 $C_{11}H_{15}N_5O$+0.5M $H_2O$ requires C, 54.5; H. 6.2; N, 28.9%). $v_{max}/cm^{-1}$ 3481 ($NH_2$), 3352 (NH), 3204 (CH), 2957 (CH), 1626 (C=C), 1581 (C=C); $\lambda_{max}$ ($CH_3OH$)/nm 282; $\delta_H$ (200 MHz, $d_6$-DMSO) 12.50 (1H, s, NH), 7.93 (1H, s, C(8)H), 6.35 (2H, s, $NH_2$), 4.38 (2H, d, J 7, $OCH_2$), 2.47 (1H, m, C(1')H), 2.0–1.2 (8H, in, C(2')H, C(3')H, C(4')H, C(5')H); m/z (+EI) 233 ($M^+$, 21%), 151 ($MH^+$—$C_6H_{11}$, 100).

Synthesis of $O^6$-(Cyclopentyl)methylguanine (NU2068)—Method B

Cyclopentanemethanol (50 mg, 5.8 mmol) was added to sodium hydride (0.35 g, 14.7 mmol) in anhydrous THF (20 ml). After 20 min, 2-amino- 6-chloropurine (0.50 g, 2.9 mmol) was added and the reaction refluxed under nitrogen for four days. The reaction was cooled, neutralised (acetic acid), the solvents removed in vacuo and the residue recrystallised from water to give the title compound as a white solid (0.42 g, 62%)(m.p. 121° C.).

$O^6$-(3'-Cyclohexenyl)methylguanine (NU2073)

3-Cyclohexene methanol (2.5 g, 22 mmol) was added to sodium hydride (1.32 g, 55 mmol) in dry THF (100 ml) and the reaction stirred under argon at room temperature for 30 min. 2-Amino-6-chloropurine (1.87 g, 11 mmol) was added and the reaction refluxed for 24 h. The resulting solution was cooled and acidified with acetic acid, the solvents removed and the residue triturated with water. Purification by flash column chromatography on silica gel, eluting with 10% methanol in dichloromethane, afforded the title compound as a white crystalline solid (2.57 g, 95%)(m.p. 176–177° C.). (Found: C, 58.0; H, 6.3; N, 27.7 $C_{12}H_{15}N_5O$+0.25M $CH_3OH$ requires C, 58.1; H, 6.3; N, 27.7%). $v_{max}/cm^{-1}$ 3340 ($NH_2$), 3200 (NH), 2900 (CH), 1620 (C=C), 1580 (C=C); $\delta_H$ (200 MHz, $d_6$-DMSO) 12.35 (1H, br s, NH), 7.76 (1H, s, C(8)H), 6.15 (2H, s, $NH_2$), 5.70 (2H, s, C(3')H, C(4')H), 4.30 (2H, d, J 7, $OCH_2$), 2.10–1.85 (6H, 3×m, C(2')H, C(5')H, C(6')H), 1.40 (1H, m, C(1')H); $\delta_C$ (50.3 MHz, $d_6$-DMSO) 160.1, 155.3, 137.9, 127.2, 125.9, 69.9, 33.1, 28.0, 25.1, 24.2; m/z (FAB) 246 ($MH^+$, 70%), 152 ($MH_2^+$—$C_7H_{11}$, 100), 95 ($C_7H_{11}$, 8).

$O^6$-(1'-Cyclopentenyl)methylguanine (NU2074)

To sodium hydride (0.57 g, 24 mmol) in anhydrous DMSO (6 ml) was added 1-cyclopentenemethanol (6.57 g, 67 mmol). After 1 h, 2-amino-trimethylpurin-6-ylammonium chloride (2.74 g, 12 mmol) was added and the reaction stirred for a further hour at room temperature. Acetic acid (2 ml) and ether (360 ml) were added to the resulting solution and the solid collected and triturated with water. The ether, DMSO and 1-cyclopentenemethanol were removed from the filtrate and the residue diluted with ether to yield a second crop. The solids were combined, dissolved in hot ethanol, filtered, the volume of solvent reduced to 10 ml and the title compound collected as a pale yellow solid (1.92 g, 70%)(m.p. 210° C.). (Found C, 57.1; H, 5.9; N, 28.0 $C_{11}H_{15}N_5O$+0.4M $CH_3CH_2OH$ requires C, 56.7; H, 6.2; N, 28.0%). $v_{max}/cm^{-1}$ $^{3460}$ ($NH_2$), 3300 (NH), 1640 (C=C), 1280 (CN), 1150 (CO); $\lambda_{max}$ ($CH_3OH$)/nm 385; $\delta_H$ (200 MHz, $d_6$-DMSO) 12.35 (1H, br s, NH), 7.75 (1H, s, C(8)H), 6.15 (2H, s, $NH_2$), 5.75 (1H, s, C(2')H), 5.00 (2H, s, $OCH_2$), 2.35 (4H, m, C(3')H, C(5')H), 1.90 (2H, q, J 7.4, C(4')H); $\delta_C$ (50.3 MHz, $d_6$-DMSO) 159.9, 140.2, 138.0, 128.2, 64.2, 32.9, 32.3, 23.1; m/z (FAB) 233 (12%), 232 ($MH^+$, 100), 231 ($M^+$, 55), 230 ($M^+$—H, 35), 152 ($M^+$—$C_6H_7$, 70).

$O^6$-(1'-Cyclohexenyl)methylguanine (NU12076)

1-Cyclohexenemethanol (2.04 g, 18.2 mmol) was added to sodium hydride (0.16 g, 6.6 mmol) in anhydrous DMSO (6 ml). After 1 h, 2-amino-trimethylpurin-6-ylammonium chloride (0.75 g, 3.3 mmol) was added and the reaction stirred for a further hour at room temperature. Acetic acid (2 ml) was added followed by ether (360 ml). After 2 h the solid was collected and triturated with water. The ether, DMSO and alcohol were removed from the filtrate which was diluted with ether to yield a second crop. The combined solids were dissolved in hot methanol, filtered, the volume of solvent reduced to 10 ml and the title compound collected as a pale yellow solid (0.57 g, 71%)(m.p. 195–197° C.). (Found C, 55.8; H, 6.0; N, 26.25 $C_{12}H_{15}N_5O$+0.85M $H_2O$ requires C, 55.3; H, 6.4; N, 26.9%). $v_{max}/cm^{-1}$ 3457 ($NH_2$), 3295 (NH), 3186 (CH), 2931 (CH), 1698 (C=C), 1631 (C=C); $\delta_H$ (200 MHz, $d_6$-DMSO) 12.50 (1H, br s, NH), 7.92 (1H, s, C(8)H), 6.33 (2H, s, $NH_2$), 5.93 (1H, s, C(2')H), 4.88 (2H, s, $OCH_2$), 2.14 and 1.68 (8H, 2×m, C(3')H and C(6')H, C(4')H and C(5')H); $\delta_C$ (50.3 MHz, $d_6$-DMSO) 159.9, 138.5, 133.7, 125.7, 69.7, 25.8, 24.8, 22.3, 22.1; m/z (+EI) 245 ($M^+$, 59%), 151 ($MH^+$—$C_7H_{11}$, 100), 134 ($M^+$—$OC_7H_{11}$, 56).

$O^6$-(S)-[4'-(Isopropen-2"-yl)-cyclohex-1'-enyl]) methylguanine (NU2077)

(s)-4-(Isopropene)cyclohex-1-enemethanol ((s)-perillyl alcohol) (3.66 g, 24 mmol) was added to sodium hydride (0.21 g, 8.8 mmol) in anhydrous DMSO (6 ml). After 1 h 2-amino-trimethylpurin-6-ylammonium chloride (1.00 g, 4.4 mmol) was added and the reaction stirred for a further hour at room temperature. Acetic acid (2 ml) was added followed by ether (360 ml). After 2 h the solid was collected and triturated with water. The ether, DMSO and alcohol were removed from the filtrate and dilution with ether yielded a second crop. The combined solids were dissolved in hot methanol, filtered, the volume of solvent reduced to 10 ml and the title compound collected as a white solid (0.79 g, 64%)(m.p. 190–192° C.). (Found C, 63.0; H, 6.4; N, 23.5 $C_{15}H_{19}N_5O$+0.2M $CH_3OH$ requires C, 62.6; H, 6.8; N, 24.0%). $v_{max}$/cm$^{-1}$ 3460 ($NH_2$), 3404 (NH), 3315 (CH), 3205 (CH), 2964 (CH), 1626 (C=C), 1584 (C=C); $\delta_H$ (200 MHz, d$_6$-DMSO) 12.50 (1H, br s, NH), 7.93 (1H, s, C(8)H), 6.35 (2H, s, $NH_2$), 5.96 (1H, s, C(2')H), 4.91 (2H, s, $CH_2$=), 4.82 (2H, s, $OCH_2$), 2.2–1.9 (6H, m, C(3')H, C(5')H and C(6')H), 1.82 (3H, s, $CH_3$), 1.60 (1H, m, C(4')H); $\delta_C$ (50.3 MHz, d$_6$-DMSO) 159.9, 149.4, 133.5, 125.1, 109.3, 69.2, 30.2, 27.2, 26.3 ,20.9; m/z (+EI) 285 (M$^+$, 19%), 151 (M$^+$—$C_{10}H_{15}$100).

$O^6$-Ribofuranosylguanine (NU6012)

Methyl-2,3-O-isopropylidene-b-D-ribofuranoside (1.23 g, 6.03 mmol) was dissolved in anhydrous DMSO (10 ml) and sodium hydride (77 mg, 3.21 mmol) was also added. The reaction mixture was left to stir at room temperature for 1 h under $N_2$ before adding 2-amino-1,4-diazabicyclo[2,2,2]octylpurin-6-ylammonium chloride (0.3 g, 1.07 mmol). This was left to react for 48 h at room temperature. The mixture was then neutralised with glacial acetic acid and DMSO was removed in vacuo. The crude product was purified by column chromatography, eluting with 10% methanol in dichloromethane to furnish a cream solid (0.0886 g, 74%), m.p 220–225° C.; $u_{max}$/cm$^{-1}$ 3460 ($NH_2$), 3201 (NH), 2937 ($CH_2$), 1627 (C=C); dH NMR (200 MHz, d$_6$-DMSO) 1.37 (3H, s, $CH_3$), 1.49 (3H, s, $CH_3$), 3.34 (3H, s, $OCH_3$), 4.50 (3H, m, $OCH_2$, C(4)H), 4.75 (1H, d, C(2)H, J=6 Hz), 4.91 (1H, d, C(3)H, J=6 Hz), 5.07 (1H,s, C(1)H), 6.41 (2H, s, $NH_2$), 7.93 (1H, s, C(8)H), 12.5 (1H, br s, NH); m/z +(EI) 337 (M$^+$, 49%),322 (M$^+$—$CH_3$, 58), 151 (MH$^+$—$C_9H_{14}O_4$, 68).

$O^6$-Tetrahydrofurfurylmethylguanine (NU6013)

Tetrahydroftriiryl alcohol (1.7 g, 16.6 mmol) and sodium hydride (0.21 g, 8.75 mmol) were added to anhydrous DMSO (8 ml). This was left to stir at room temperature for 1 h under $N_2$. 2-Amino-6-chloropurine (0.5 g, 2.95 mmol) was then added and the mixture was heated at 1 00° C. for 48 h. The reaction mixture was neutralised with glacial acetic acid and DMSO was removed in vacuo. The crude product was columned using 10% methanol in dichloromethane and the product was obtained but NMR showed contamination by 2-amino-6-chloropurine.

This mixture was thus suspended in anhydrous DMSO (14 ml) and 1,4-diazabicyclo[2,2,2]octane (0.358 g, 3.2 mmol) was added. The reaction mixture was then stirred at room temperature for 12 h. DMSO was removed in vacuo and the crude product was purified by column chromatography, eluting with 20% methanol in dichloromethane. The title compound was obtained as a cream solid (0.295 g, 43%), m.p. 224–228° C.; (Found: C, 51.06; H, 5.53; N, 29.79% $C_{10H13}N_5O_2$ and 0.01 M $CH_2Cl_2$ requires C, 50.93; H. 5.52; N, 29.67%); $u_{max}$/cm$^{-1}$ 3331 (NH), 2976 ($CH_2$), 2550 ($NH_2$), 1625 (C=C), 1580 (NH); dH NMR (200MHz, d$_6$-DMSO) 1.93 (4H, m, $C_4H_7O$), 3.84 (2H, m, $C_4H_7O$), 4.34 (1H, m, C(1)H), 4.47 (2H, d, J=4.5 Hz, $OCH_2$), 6.36 (2H, s, $NH_2$), 7.9 (1H, s, C(8)H), 12.6 (1H, br s, NH); m/z (+EI) 249 (M$^+$, 51%), 165 (MH$^+$, $C_4H_7O$, 42), 151 (MH$^+$—$C_5H_9O$, 78), 134 (M$^+$—$C_5H_9O_2$, 20), 78 (31).

$O^6$-Adamantylmethylguanine (NU6014)

1-Adamantanemethanol (1.374 g, 8.3 mmol) was dissolved in anhydrous DMSO (10 ml) and sodium hydride was then added. The reaction mixture was left to stir under $N_2$ at room temperature for 1 h. 2-Amino-6-chloropurine (0.25 g, 1.48 mmol) was then added to the reaction mixture and this was heated at 100° C. for 4 days. The reaction mixture was then cooled and subsequently neutralised with glacial acetic acid, the solvents were then removed. Purification of the crude product was achieved by column chromatography using 10% methanol in dichloromethane as the eluting solvent. The desired product was isolated as a cream solid in low yield (0.04 g, 10%), m.p. 260–265° C.; (Found: C, 61.6; H, 6.51; N, 22.44% $C_{16}H_{21}N_5O$ and 0.7 M $H_2O$ requires C, 61.6; H, 7.19: N, 22.46%); $u_{max}$/cm$^{-1}$ 3315 (NH), 2900 ($CH_2$), 2573 ($NH_2$), 1622 (C=C), 1584 (NH); dH NMR (200 MHz, d$_6$-DMSO) 1.92 (16H, m, $C_{10}H_{16}$), 4.11 (2H, s, $OCH_2$), 6.35 (2H, s, $NH_2$), 7.90 (1H, s, C(8)H), 12.46 (1H, br s, NH); mlz (+EI) 299 (M$^+$, 100%), 151 (M$^+$—$C_{11}H_{16}$, 44), 135 (M$^+$—$C_{11}H_{16}O$, 20).

$O^6$-Galactosylguanine (NU6017)

1,2:3,4-Diisopropylidene-a-D-galactopyranose (1.56 g, 6 mmol) and sodium hydride (0.078 g, 3.25 mmol) were added to anhydrous DMSO (10 ml) and reacted for 1 h at room temperature. 2-Amino-1,4-diazabicyclo[2,2,2]-octylpurin-6-ylammonium chloride (0.3 g, 1.07 mmol) was then added and the reaction mixture was stirred at room temperature for 48 h before being neutralised with glacial acetic acid. The solvents were removed in vacuo. The crude product was columned in 10% methanol in dichloromethane and then recrystallised from ethyl acetate/petrol. The desired product was furnished as a white solid in reasonable yield (0.2256 g, 54%), m.p. 147–149° C.; (Found: C, 51.9; H, 5.8; N, 17.81% $C_{17}H_{23}N_5O_6$ and 0.01 M $CH_2Cl_2$ requires C, 51.8; 11, 5.84; N, 17.77%); $u_{max}$/cm$^{-1}$ 3459 ($NH_2$), 3200 (NH), 2936 ($CH_2$), 625 (C=C); dH NMR (200 MHz, d$_6$-DMSO) 1.39 (6H, d, 2'$CH_3$), 1.48 (6H, s, 2'$CH_3$), 4.27 (1H, m, C(5)H), 4.45 (3H, m), 4.61 (1H, dd, J=7Hz), 4.74 (1H, dd, J=7 Hz), 5.59 (1H, d, J=5 Hz), 6.39 (2H, s, $NH_2$), 7.91 (1H, s, C(8)H), 7.95 (1H, br s, NH); m/z (+EI) M$^+$(393, 58%), M$^+$—$CH_3$ (378, 45), 351 (4), M$^+$—$C_{11}H_{16}O_5$ (165, 14), 151 (100), 93 (11), 43 (63).

2-Amino-6-(2-naphthyl)methylguanine (NU6018)

2-Naphthalenemethanol (0.8g, 5 mmol) and sodium hydride (0.065g, 2.71 mmol) were added to anhydrous DMSO (10 ml). After 1 h 2-amino-1,4-diazabicyclo[2,2,2] octylpurin-6-ylammonium chloride (0.25g, 0.89 mmol) was added to the reaction mixture and this was stirred at room temperature for 5 days. The reaction mixture was neutralised with glacial acetic acid (0.1 ml), and the solvents were then removed. The crude product was purified by column chromatography using a solvent system of 10% methanol in dichloromethane. Title product was isolated as a cream solid (0.0645 g. 25%), m.p. 230–234° C.; (Found: C, 66; H, 4.47; N, 24.05% $C_{16}H_{13}N_5O$ and 0.01 M $CH_2Cl_2$ M requires C, 65.83; H, 4.46; N, 23.98%); $u_{max}$/cm$^{-1}$ 3335 (NH), 2939 ($CH_2$), 2562 ($NH_2$), 1642 (C=C). 1585 (NH); dH NMR (200 MIfz, d$_6$-DMSO) 5.75 (2H, s, $OCH_2$), 6.44 (2H, br s, $NH_2$), 7.68 (3H, m, $C_{10}H_7$), 8.04 (5H, m, C(8)H and $C_{10}H_7$);

m/z (+EI) 291 (M$^+$, 53%), 141 (C$_{11}$H$_9$$^+$,100), 95 (8), 81 (16).

O$^6$-Tetrahydropyranylmethylguanine (NU6019)

Tetrahydropyran-2-methanol (0.235 g, 2.02 mmol) was added with sodium hydride (0.026 g, 1.08 mmol) to anhydrous DMSO (8 mi) and was left to stir under N$_2$ for 1 h at room temperature. 2-Amino-1,4-diazabicyclo[2,2,2]-octylpurin-6-ylammonium chloride (0.1 g, 0.36 mmol) was then added to the reaction mixture and this was left to stir for 48 h. The mixture was then neutralised with glacial acetic acid and the solvents were removed. Purification of the crude product was achieved by column chromatography, eluting with 10% methanol in dichloromethane. The title product was achieved in good yield as a cream solid (0.05127 g, 62%), m.p. 255–260° C.; (Found: C, 53.0; H, 6.0; N, 28.1% C$_{11}$H$_{15}$N$_5$O$_2$ and 0.01 M CH$_2$Cl$_2$ require C, 52.88; H, 6.01; N, 28.01%); u$_{max}$/cm$^{-1}$ 3336 (NH), 2940 (CH$_2$), 2563 (NH$_2$), 1626 (C=C), 1587 (NH); dH NMR (200 MHz, d$_6$-DMSO) 1.63 (6H, m, C$_5$H$_9$O), 3.50 (1H, m, C$_5$H$_9$O), 3.76 (1H, m, ax C(1)H), 3.99 (1H, m, equat C(5)H), 4.44 (2H, m, OCH$_2$), 6.37 (2H, s, NH$_2$), 7.92 (1H, s, C(8)H), 12.5 (1H, br s, NH); m/z (+EI) 249 (M$^+$, 34%), 165 (M$^+$—C$_5$H$_8$O, 26), 151 (M$^+$—C$_6$H$_{11}$O, 100).

2-Amino-6-(1-naphithyl)methylguanine (NU6020)

1-Naphthalenemethanol (0.096g, 6.1 mmol) and sodium hydride (0.078 g, 3.25 mmol) were added to anhydrous DMSO (8 ml) and left to stir at room temperature for 1 h. 2-Amino-1,4-diazabicyclo[2,2,2]octylpurin-6-ylammonium chloride (0.3 g, 1.1 mmol) was then added to the reaction mixture and stirred under N$_2$ at room temperature for 4 days. The mixture was then neutralised with glacial acetic acid and the solvents were removed in vacuo. Purification of the crude product was achieved by column chromatography, eluting with 10% methanol in dichloromethane. The title product was furnished as a pale yellow solid(0.1773 g, 57%), m.p. 165–170° C.; (Found: C, 63.94; H, 4.55; N, 22.6% C$_{16}$H$_{15}$N$_5$O and 0.01 M CH$_2$Cl$_2$ requires C, 65.83; H, 4.46; N, 23.98%); u$_{max}$/cm$^{-1}$ 3424 (NH), 2971 (CH$_2$), 2638 (NH$_2$), 1635 (C=C), 1579 (NH); dH NMR (200 MHz, d$_6$-DMSO) 1.92 (16H, m, C$_{10}$H$_{16}$), 4.11 (2H, s, OCH$_2$), 6.35 (2H, s, NH$_2$), 7.90 (1H, s, C(8)H), 12.46 (1H, br s, NH); m/z (+EI) 291 (M$^+$, 17%), 141 (C$_{11}$H$_8$$^+$, 90), 81(45).

O$^6$-(2,2-Dimethyl-1,3-dioxolane-4-methoxy)guanine (NU6021)

2,2-Dimethyl-1,3-dioxolane-4-methanol (0.079 g, 5.98 mmnol) was added to anhydrous DMSO (8 ml) with sodium hydride (0.08 g, 3.33 mmol). This was left to stir for 1 h at room temperature before adding 1,4-diaza-bicyclo[2,2,2]octylpurin-6-ylammonium chloride (0.3 g, 1.07 mmol) to the reaction mixture. The reaction was stirred under N$_2$ for 5 days at room temperature and was subsequently neutralised with glacial acetic acid before the solvents were removed by short path distillation. The crude product was purified by column chromatography, eluting with 10% methanol in dichloromethane which yielded the title compound as a cream solid in good yield (0.2466 g, 87%); (Found: C, 47.49; H, 6.21; N, 24.42% C$_{11}$H$_{15}$N$_5$O$_3$ requires 0.15 M CH$_3$OH and 0.75 M H$_2$O C, 47.23; H, 6.04; N, 24.71%), m.p. 170–172° C.; u$_{max}$/cm$^{-1}$ 3197 (NH), 2942 (CH$_2$), 1626 (C=C); dH NMR (200 MHz, d$_6$-DMSO) 1.38 (3H, s, CH$_3$), 1.44 (3H, s, CH$_3$), 3.84 (1H, dd, C(3)H), 4.18 (1H, dd, C(3)H), 4.48 (3H, m, OCH$_2$, C(2)H), 6.35 (2H, br s, NH$_2$), 7.91 (1H, s, C(8)H); dC (50 MHz, d$_6$-DMSO) 25.69 (Me), 26.96 (Me), 66.12, 66.46, 73.82 (OCH$_2$), 109.19, 159.93; m/z M$^+$(265, 28%), M$^+$—CH$_3$ (250, 47), MH$^+$—C$_6$H$_{11}$O$_2$ (151, 100).

O$^6$-(1,4-Dioxaspiro[4.5]decane-2-methoxy)guanine (NU6022)

(+)-1,4-Dioxaspiro[4.5]decane-2-methanol (0.858 g, 3.9mmol) and sodium hydride (0.065 g, 2.71 mmol) were added to anhydrous DMSO (8 ml) and left to stir at room temperature for 1 h. I ,4-Diazabicyclo[2,2,2]octylpurin-6-ylammonium chloride (0.25 g, 0.89 mmol) was then added to the reaction mixture and this was left to stir at room temperature for 5 days. The mixture was neutralised with glacial acetic acid and solvents were removed in vacuo. Purification of the crude product by column chromatography using 10% methanol in dichloromethane furnished the desired product as a cream solid in good yield (0.251 g, 92%), m.p. 214–218° C.; (Found: C, 54.49; H, 6.38; N, 22.5% C$_{14}$H$_{19}$N$_5$O$_3$ and 0.05 M CH$_2$Cl$_2$ requires C, 54.52; H, 6.18; N, 22.64%); u$_{max}$/cm$^{-1}$ 3477 (NH$_2$), 3182 (NH), 2937 (CH$_2$), 1618 (C=C); dH NMR (200 MHz, d$_6$-DMSO) 1.60 (10H, m, C$_5$H$_{10}$), 3.86 (1H, dd, C(3)H), 4.19 (1H, dd, C(3)H). 4.53 (3H, m. OCH9, C(2)H), 6.37 (2H. br s, NH$_2$), 7.94 (1H, s, C(8)H); dC (50 MHz, d$_6$-DMSO) 23.74, 23.91. 24.94, 34.92, 36.31. 65.87, 66.55, 73.51 (OCH$_2$), 109.64, 138.73, 159.92; m/z M$^+$(305, 29%), MH$^+$—C$_6$H$_{10}$0 (208, 7), MH$^+$—C$_9$H$_{15}$ (151, 86).

In the further examples hereinafter described of the preparation of O$^6$-Alkylguanine derivatives in accordance with the invention, the general synthetic procedure unless otherwise stated was as follows:

The appropriate alcohol (5.6 mmol) was added to a suspension of sodium hydride (0.08 g, 3 mmol) in anhydrous DMSO (8 ml), and the reaction mixture was stirred under nitrogen at room temperature for 1 h. 1,4-Diazabicyclo[2, 2,2]octane purine ('DABCO-purine', 0.3 g, 1.07 mmol) was added and the reaction was, stirred for 5 days under a nitrogen atmosphere at ambient temperature. The reaction mixture was neutralised with glacial acetic acid and the solvents were removed in vacuo. The residual product was purified by column chromatography on silica, employing dichloromethane: methanol (9:1) as eluent.

2-amino-6-cyclohexylethyloxypurine (NU6023)

The title compound was isolated in a yield of 82%, 0,23 g; mp 209.5° C.; (Found: C, 59.78; H, 7.24; N, 26.83. Calc. for C$_{13}$H$_{19}$N$_5$O: C, 59.77; H, 7.28; N, 26.82%); δH (200 MHz, d$_6$-DMSO) 1.02 (2H, m, CH$_2$). 1.20–1.30 (11H, m), 4.518 (2H, t, OCH$_2$), 6.287 (2H, br-s, NH$_2$), 7.906 (1H, s, C(8)H), 12.503 (1H, br-s, NH); m/z (EI) 261 (M$^+$).

2-amino-6-[(R)-2',2'-dimethyl-1',3'-dioxolane-5'-methyl]oxypurine (NU6024)

The title compound was obtained in a yield of 98%, 0.28 g; mp 190.4° C. (Found: C, 48.17; H, 5.81; N, 25.57. Calc. for C$_{11}$H$_{15}$N$_5$O$_3$.0.5 mole H$_2$O: C, 48.17; H, 5.88; N, 25.53%); δH (200 MHz, d$_6$-DMSO) 1.409 (6H, d, 2×CH$_3$), 3.863 (1H, m), 4.209 (1H, m), 4.576 (3H, m), 6.378 (2H, br-s. NH$_2$), 7.939 (1H, s, C(8)H), 12.5 (1H, br-s,. NH); m/z (EI) 265 (M$^+$).

2-amino-6-[(S)-2',2'-dimethyl-1',3'-dioxolane-5'-methyl]oxypurine (NU6025)

The required product was obtained in a yield of 98%, 0.28 g; m.p. 166.7 C; (Found: C, 49.65; H, 5.66; N, 26.04. Calc.

for $C_{11}H_{15}N_5O_3$: C, 49.81; H, 5.66; N, 26.42%); δH (200 MHz, $d_6$-DMSO) 1.411 (6H, d, 2×$CH_3$), 3.904 (1H, m), 4.200 (1H, m), 4.596 (3H, m), 6.370 (2H, br-s, $NH_2$), 7.946 (1H, s, C(8)H), 12.600 (1H, br-s, NH); mn/z (EI) 265 ($M^+$).

2-amino-6-[1',4'-benzodioxanyl-2'-methyl]oxypurine (NU6026)

The product was obtained in a 62% yield, 0.20 g; m.p. 184.5° C.; (Found: C, 56.13; H, 4.36; N, 23.12. Calc. for $C_{14}H_{13}N_5O_3$: C, 56.19; H, 4.35; N, 23.41%); δH (200 MHz, $d_6$-DMSO) 4.252 (1H, m), 4.510 (1H, m), 4.797 (3H, m), 6.401 (2H, br-s, $NH_2$), 7.001 (4H, m), 7.959 (1H, s, C(8)H), 12.592 (1H, br-s, NH); m/z (EI) 299 ($M^+$).

2-Amino-6-(3'-pyridyl)methyloxypurine (NU6029)

Obtained as a cream solid in a yield of 70%, 0.18 g; (Found: C, 52.93; H, 3.76; N, 30.96% $C_{11}H_{10}N_6O$ and 0.5 M $CH_3CO_2H$ requires C, 52.94; H, 4.41; N, 30.88%); 6H (200 MHz, $d_6$-DMSO) 5.61 (2H, s, $OCH_2$), 6.44 (2H, br s, $NH_2$), 7.53 (1H, m, C(2)H), 7.94 (1H, s, C(8)H), 8.04 (1H, m, C(1)H), 8.65 (1IH, m, C(3)H), 8.85 (11H, m, C(4)H); m/z (+EI) 242 ($M^+$, 100%), 150 ([M—$C_6H_6N$]+, 12), 134 ([M—$C_6H_7NO$]+, 91 (29).

2-amino-6-(2'-methylnorbornyl)methyloxypurine (NU6030)

The desired product was obtained as a cream solid in 5 1% yield, 0.15 g; $δ_H$ (200 MHz, $d_6$-DMSO) 0.99–2.2 (13H, m, $C_6H_{13}$), 4.28 (2H, d, $OCH_2$), 4.33–4.53 (1H, m) 6.28 (2H, br s, $NH_2$), 7.90 (11H, s, C(8)H); m/z (+EI) 273 ($M^+$, 12%), 151 ([$MH^+$—$C_9H_5O$], 100), 81 (16), 55 (18).

2-amino-6-[(S)-2'-oxopyrrolidin-5'-methyl] oxypurine (NU6031)

The title compound was obtained in 87% yield, 0.23 g; m.p. 150.9° C.; (Found: C, 43.52; H. 5.14; N, 30.13. Calc. for $C_{10}H_{12}N_6O_2 \cdot 1.5$ mole $H_2O$: C, 43.63; H, 5.49; N. 30.53%); 8H (200 MHz, $d_6$-DMSO) 2.006 (1H, m), 2.304 (3H, m), 4.005 (11H, m), 4.434 (2H, d, $CH_2$), 6.337 (2H, br-s, NH12), 7.926 (2H, br-s, C(8)H & NH); m/z (EI) 248 ($M^+$).

2-amino-6-[(R)-2'-oxopyrrolidin-5'-methyl] oxypurine (NU6032)

After recrystallising from methanol, yield of 46%, 0.12 g; m.p. 147.8° C.; (Found: C, 44.85; H, 5.19; N, 31.19. Calc. for $C_{10}H_{12}N_6O_2 \cdot 1$ mole H2O: C, 45.11; H, 5.30; N, 31.56%); δH (200 MHz, $d_6$-DMSO) 2.006 (1H, m), 2.367 (3H, m), 4.062 (1H, m), 4.451 (2H, d, $CH_2$), 6.337 (2H, br-s, $NH_2$), 7.923 (2H, br-s, C(8)H & NH); m/z (EI) 248 ($M^+$).

2-Amino-6-cyclohexylmethyloxy-8-oxopurine (NU6033)

A solution of 2,5,6-triamino-4-cyclohexylmethyloxypyrimidine (1.0 g, 4.24 mmol) and 1,1'-carbonyldiimidazole (0.69 g, 4.24 mmol) in anhydrous DMF (5 ml) was stirred under nitrogen at ambient temperature for 48 h. Addition of water (100 ml) afforded a white solid which was collected by filtration, redissolved in 2 M sodium hydroxide solution (200 ml), and filtered. The filtrate was neutralised with glacial acetic acid and allowed to stand at 4° C. for 2 h, when the precipitate which deposited was collected and washed thoroughly with water. Recrystallisation from aqueous ethanol yielded the required product (0.65 g, 58%), m.p. 297° C.; (Found: C. 54.66; H, 6.47;. N, 26.63% $C_{12}H_{17}N_5O_2$ requires C, 54.75; H, 6.46; N, 26.62%); δH (200 MHz, $d_6$-DMSO) 1.04–1.39 (δH, m, $C_6H_{11}$), 1.76–1.90 (6H, m, $C_6H_{11}$), 4.17 (2H, $OCH_2$, J=6.53 Hz), 6.15 (2H. br s, $NH_2$), 10.49 (1H, br s, NH), 1 1.09 (1H, br s, NH); m/z (+EI) 263 ($M^+$, 75%), 167 ($MH^+$—$C_7H_{13}$, 100), 81 (6), 69 (7).

2-Amino-6-benzyl-8-oxoguanine (NU6043)

2,5,6-Triamino-4-benzyloxypyrimidine (0.05 g, 0.22 mmol) and 1,1'-dicarbonyldiimidazole (0.04 g, 0.216 mmol) were dissolved in anhydrous DMF under nitrogen. The reaction mixture was stirred at ambient temperature for 48 h, and a further portion of 1,1'-carbonyldiimidazole (0.04 g, 0.216 mmol) was added. After stirring for a further 24 h, water (50 ml) was added and the cream precipitate which developed was collected. The collected solids were redissolved in 2 M sodium hydroxide solution and, after filtration, the solution was neutralised with glacial acetic acid and stood at 4° C. for 12 h. The yellow precipitate which deposited was collected and washed thoroughly with water. Recrystallisation from aqueous methanol furnished the desired product (0.05 g, 84%), m.p. 316° C. (decomposed); $δ_H$ (200 MHz, $d_6$-DMSO) 5.53 (2H, s, $OCH_2$), 6.29 (2H, br s, $NH_2$), 7.49–7.60 (δH, m, $C_6H_5$); m/z (+EI) 257 ($M^+$, 34%), 91 (100), 65 (9).

2-Chloro-6-cyclohexylmetboxypurine (NU6047)

To a solution of sodium (0.18 g, 7.94 mmol) in cyclohexylmethanol (10 ml) at 90° C. under nitrogen, was added 2,6-dichloropurine (0.5 g, 2.645 mmol). After stirring for 90 min the mixture was cooled to room temperature, neutralised with glacial acetic acid and the volatile solvents were removed under reduced pressure. The residual solid was triturated with water and filtered, (0.6 g, 85%); δH (200 MHz, $d_6$-DMSO) 1.232 (δH, br-m), 1.877 (6H, br-m), 4.345 (2H, d, $OCH_2$), 7.991 (1H, s, C(8)H); m/z (EI) 266 ($M^+$).

6-Cyclohexyimethoxy-2-N,N-dimethylaminopurine (NU6048)

To a solution of 2-chloro-6-cyclohexylmethoxypurine (0.15 g, 0.56 mmol) in DMF (3 ml) was added 2-aminoethanol (0.12 ml, 1.95 mmol), and the reaction mixture was stirred at 90° C. for 3 days. The solvents were removed in vacuo and the residual product was purified by column chromatography on silica gel, using dichloromethane: methanol (9:1) as eluent. Recrystallisation from ethyl acetate gave further purification and afforded the title compound (98 mg, 63% yield); δH (200 MHz, $d_6$-DMSO) 1.216 (5H, br-m), 1.918 (6H, br-m), 3.307 (6H, s, $N(CH_3)_2$), 4.350 (2H, d, $OCH_2$), 7.951 (1H, s, C(8)H), 12.8 (1H, br-s, NH); m/z (EI) 275 ($M^+$).

BRIEF SUMMARY

The present invention should be regarded overall as comprising each and every novel feature or combination of features disclosed herein but the main aspects of the invention comprise, principally but not exclusively, broadly the following:

(i) Novel compounds of formula (I) as defined herein;
(ii) Compounds of formula (II) with substituents as hereinbefore defined (including pro-drug forms and salts thereof) for therapy or for use in medicine and in the manufacture of medical preparations, useful for example as CDK inhibitors in treatment of cancer or other cell proliferation disorders.

(iii) Processes for the preparation of novel compounds of formula (I) as defined herein, including any novel intermediate compounds produced in carrying out such processes;

(iv) Pharmaceutical compositions or formulations comprising a compound of formula (I) as defined herein together with a pharmaceutically acceptable carrier therein; and (v) Processes for the preparation of a pharmaceutical formulation as defined in (iv) above, e.g. by methods referred to herein.

TABLE 1

| Number | Name | Structure | IC$_{50}$ ($\mu$M) or % inhibition | | |
|---|---|---|---|---|---|
| | | | CDK1 | CDK2 | CDK4 |
| Ref. | Olomoucine | 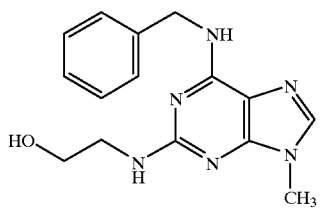 | 7 | 7<br>72 ± 2<br>at 10 $\mu$M<br>(9)<br>5.7, 5.4 | >1000 |
| NU2002 | 6-benzyloxypurine<br>C$_{12}$H$_{10}$N$_4$O<br>MW = 214.0 | 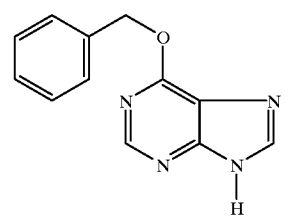 | 51 | | |
| NU2004 | 2-amino-6-methoxypurine<br>(O$^6$-methylguanine)<br>C$_6$H$_7$N$_5$O<br>MW = 165.0 | 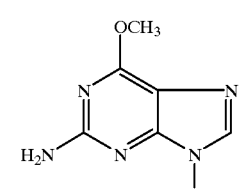 | 200 | | |
| NU2005 | 2-amino-6-benzyloxypurine<br>(O$^6$-benzylguanine)<br>C$_{12}$H$_{12}$N$_5$O<br>MW = 241.0 | 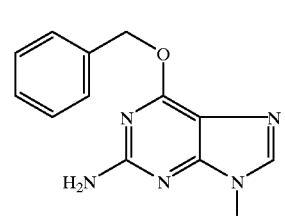 | 35 | >100<br>64 ± 3 at<br>100 $\mu$M<br>(3)<br>28.6 | 100 |
| NU2013 | 6-allyloxypurine<br>C$_{11}$H$_{16}$N$_4$O$_3$<br>MW = 176.0 | 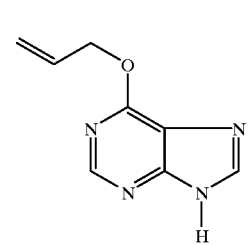 | 110 | >100 | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU2014 | 6-(2-tetrahydropyranyl-methyloxy)purine<br>C$_{11}$H$_{14}$ClN$_4$O$_2$<br>MW = 234.0 | 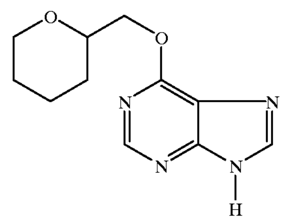 | | >100 | |
| NU2017 | 6-cyclohexylmethoxypurine<br>C$_{12}$H$_{16}$N$_4$O<br>MW = 232.0 | 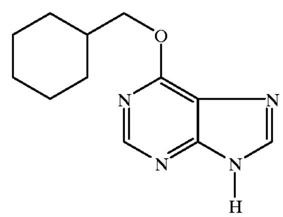 | 16 | >100<br>61 ± 2 at<br>100 $\mu$M<br>(3)<br>15.5 | |
| NU2023 | 6-(2-phenyl)ethoxypurine<br>C$_{13}$H$_{12}$N$_4$O<br>MW = 240.0 | 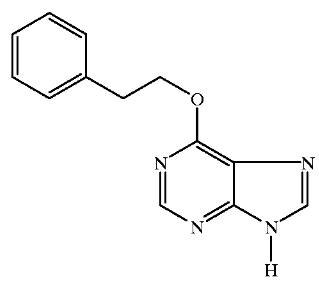 | 130 | | |
| NU2028 | 2-amino-6-allyloxypurine<br>(O$^6$-allylguanine)<br>C$_{11}$H$_{17}$N$_5$O$_3$<br>MW = 191.0 | 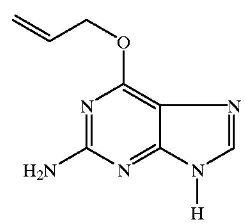 | 50 | >100 | >100 |
| NU2031 | 2-amino-6-propargyl-oxypurine<br>(O$^6$-propargylguanine)<br>C$_8$H$_7$N$_5$O<br>MW = 189.0 | 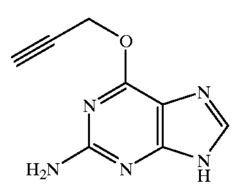 | 60 | | |
| NU2032 | 2-amino-6-(2,2-diethoxy)propoxypurine<br>C$_{12}$H$_{19}$N$_5$O$_3$<br>MW = 281.0 | 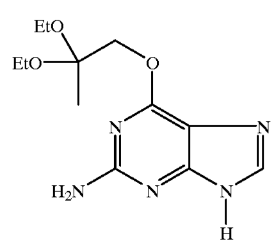 | | >100 | |

TABLE 1-continued

| | | | IC$_{50}$ ($\mu$M) or % inhibition | | |
|---|---|---|---|---|---|
| Number | Name | Structure | CDK1 | CDK2 | CDK4 |
| NU2033 | 2-amino-6-(2-oxo-2-phenyl)ethoxypurine (O$^6$-phenacetonylguanine) C$_{13}$H$_{11}$N$_5$O$_2$ MW = 269.0 | | 100 | | |
| NU2034 | 2-amino-6-(2-methyl-allyloxy)purine ('O$^6$-methallyguanine') C$_9$H$_{11}$N$_5$O MW = 205.0 | | 32 | | |
| NU2035 | 2-amino-6-(2-oxo)propoxypurine (O$^6$-acetonylguanine) C$_8$H$_9$N$_5$O$_2$ MW = 207.0 | | 100 | | |
| NU2036 | 2-amino-N9-allyl-6-allyloxypurine C$_{11}$H$_{13}$N$_5$O MW = 231.0 | | >1000 | | |
| NU2037 | 2-amino-N7-allyl-6-allyloxypurine C$_{11}$H$_{13}$N$_5$O MW = 231.0 | | >1000 | | |

TABLE 1-continued

| Number | Name | Structure | CDK1 | CDK2 | CDK4 |
|---|---|---|---|---|---|
| | | | \multicolumn{3}{c}{IC$_{50}$ ($\mu$M) or % inhibition} |
| NU2038 | 2-amino-6-allyloxy-N9-benzylpurine<br>C$_{15}$H$_{15}$N$_5$O<br>MW = 281.0 | 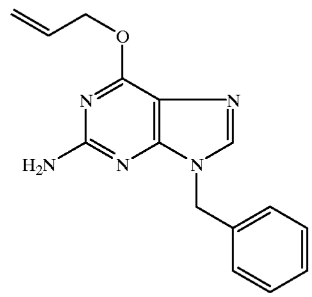 | >1000 | | |
| NU2040 | 2-amino-6-(2,3-dihydroxy)propoxypurine<br>C$_8$H$_{11}$N$_5$O$_3$<br>MW = 223.0 | 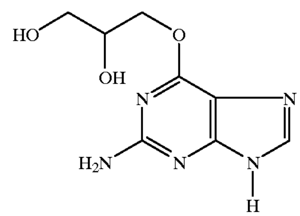 | | >100 | |
| NU2041 | 2-amino-6-(2-phenyl)ethoxypurine<br>(O$^6$-phenethoxyguanine)<br>C$_{13}$H$_{13}$N$_5$O<br>MW = 253.0 | 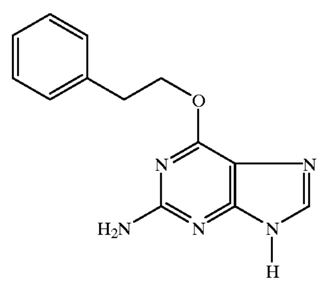 | 100 | >100 | |
| NU2042 | 2-amino-6-(2-phenylallyl-oxy)purine<br>(O$^6$-phenylallylguanine)<br>C$_{14}$H$_{13}$N$_5$O<br>MW = 267.0 | 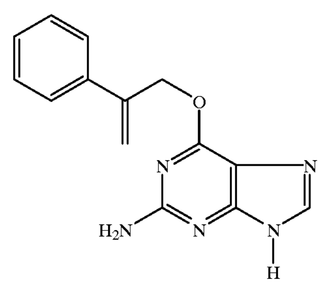 | 40 | >100<br>75 ± 2 at<br>100 $\mu$M<br>(3)<br>23.3 | >100*<br>330 |
| NU2044 | 2-amino-6-(2,3-dimethoy)propoxypurine<br>C$_9$H$_{13}$N$_5$O$_3$<br>MW = 239.2 | 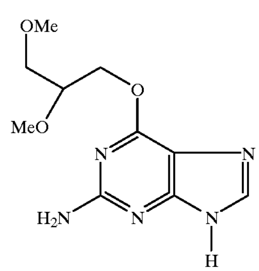 | | >100 | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU2045 | 2-amino-6-propoxypurine ('O$^6$-propylguanine') C$_8$H$_{11}$N$_5$O MW = 193.2 | 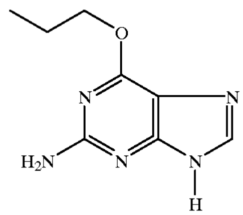 | 50 | | |
| NU2046 | 2-amino-6-ethoxypurine ('O$^6$-ethylguanine') C$_7$H$_9$N$_5$O MW = 179.2 | 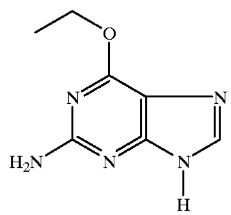 | 100 | | |
| NU2048 | 2-(N,N-dimethyl)amino-6-allyloxypurine C$_{10}$H$_{13}$N$_5$O MW = 219.0 | 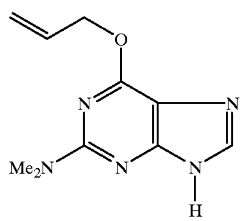 | 22 | | |
| NU2050 | 2-amino-6-(2,2-dimethoxy)butyloxypurine C$_{11}$H$_{17}$N$_5$O$_3$ MW = 267.28 | 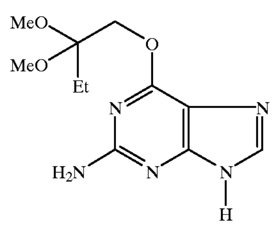 | | >100 | |
| NU2051 | 6-allyloxy-2-chloropurine C$_8$H$_7$ClN$_4$O MW = 210.62 | 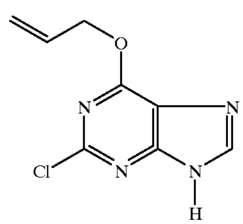 | 400 | | |
| NU2052 | 2-amino-6-n-butoxypurine ('O$^6$-butylguanine') C$_9$H$_{13}$N$_5$O MW = 207.24 | 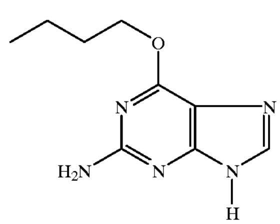 | 30 | | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU2053 | 2-amino-6-(3-methyl)butyloxypurine<br>C$_{10}$H$_{14}$N$_5$O<br>MW = 220.25 | 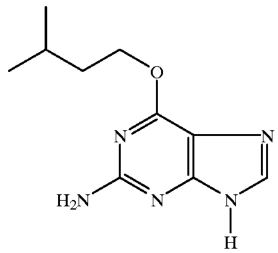 | 18 | >100* | 70 |
| NU2054 | 2-amino-6-(1-ethyl)allyl-oxypurine<br>('O$^6$-ethallylguanine')<br>C$_{10}$H$_{13}$N$_5$O<br>MW = 219.25 | 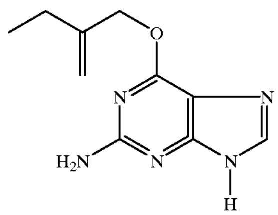 | 20 | | |
| NU2055 | 2-amino-6-isopropallyl-oxypurine<br>('O$^6$-isopropallylguanine')<br>C$_{11}$H$_{15}$N$_5$O<br>MW = 233.28 | 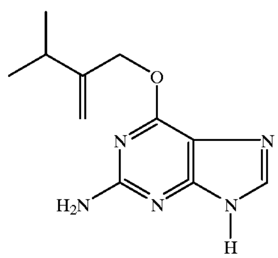 | 13 | | |
| NU2056 | 2-amino-6-(3-methyl-2-oxo)butyloxypurine<br>C$_{12}$H$_{14}$N$_5$O$_2$<br>MW = 349.27 | 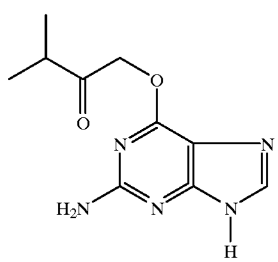 | 22 | >100<br>33 ± 2 at<br>100 $\mu$M<br>(3) | 122 |
| NU2057 | 2-amino-6-(3-methyl-2-oxo)butyloxypurine ethylene acetal<br>C$_{12}$H$_{17}$N$_5$O$_3$<br>MW = 279.30 | 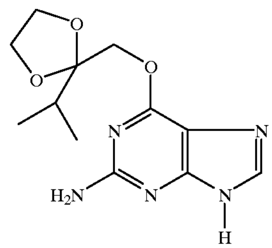 | 105 | >100 | |
| NU2058 | 2-amino-6-cyclohexyl-methyloxypurine<br>('O$^6$-cyclohexylguanine')<br>C$_{12}$H$_{17}$N$_5$O<br>MW = 247.30 | 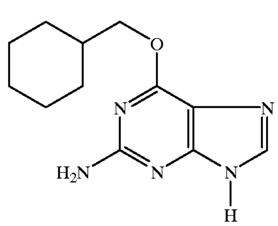 | 5,8 | >100*<br>86 ± 1 at<br>10 $\mu$M (3)<br>15.8, 11 | 38 |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU2061 | 2-amino-6-hex-5Z-enyloxypurine<br>C$_{11}$H$_{15}$N$_5$O<br>MW = 233.27 | 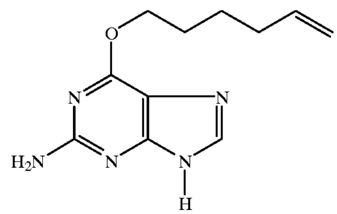 | 12 | | |
| NU2064 | 2-amino-6-heptyloxypurine<br>('O$^6$-heptylguanine')<br>C$_{12}$H$_{19}$N$_5$O<br>MW = 249.3 | 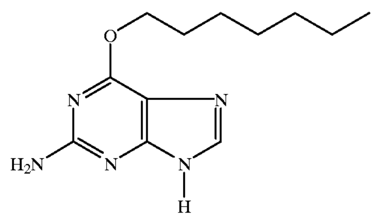 | 31 | | |
| NU2067 | 2-amino-6-hex-3E-enyloxypurine<br>C$_{11}$H$_{15}$N$_5$O<br>MW = 233.27 | 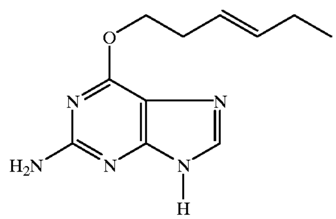 | 38 | | |
| NU2068 | 2-amino-6-cyclopentyl-methyloxypurine<br>('O$^6$-cyclopentylguanine')<br>C$_{11}$H$_{15}$N$_5$O<br>MW = 233.27 | 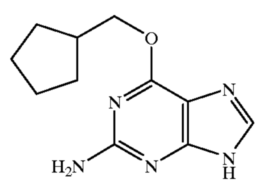 | 30 | >100 | 34 |
| NU2073 | 2-amino-6-cyclohex-3-enylmethyloxypurine<br>C$_{12}$H$_{15}$N$_5$O<br>MW = 245.28 | 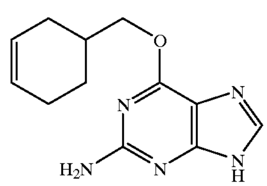 | 3.2 | 98<br>87 ± 1 at<br>100 $\mu$M<br>(3)<br>18.8 | 53 |
| NU2074 | 2-amino-6-cyclopent-1-enylmethyloxypurine<br>('O$^6$-Cyclopentenyl-guanine')<br>C$_{11}$H$_{13}$N$_5$O<br>MW = 231.25 | 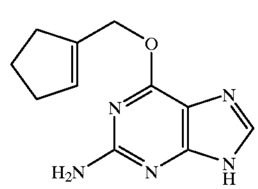 | 7 | | |
| NU2076 | 2-amino-6-(2-cyclohexenyl)-methyloxypurine<br>('O$^6$-Cyclohexenyl guanine')<br>C$_{12}$H$_{15}$N$_5$O<br>MW = 245.28 | 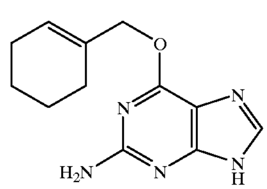 | 8 | | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU2077 | 2-amino-6-perillyl--oxymethylpurine<br>C$_{15}$H$_{19}$N$_5$O<br>MW = 285.34 | 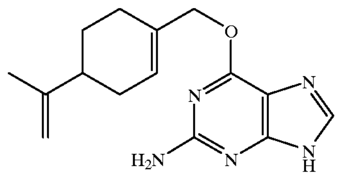 | 22 | >100 insol at 100 $\mu$M<br>16 ± 26 at 10 $\mu$M (3)<br>54% at 25 $\mu$M | >100 |
| NU2081 | 2-amino-6-(2,2-dimethoxy)-2-phenylethyloxypurine<br>C$_{15}$H$_{17}$N$_5$O$_3$<br>MW = 315.33 | 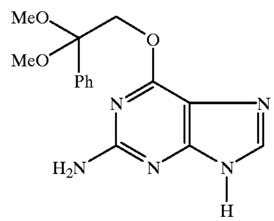 | | >100 | |
| | 2-amino-6-(2-furanyl)-methyloxypurine<br>C$_{10}$H$_9$N$_5$O$_2$<br>MW = 231.21 | | 75 | | |
| NU6012 | C$_{14}$H$_{19}$N$_5$O$_5$<br>MW = 337.33 | 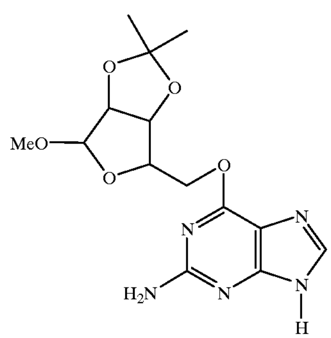 | 32% at 100 $\mu$M | >100<br>16 ± 5 at 100 $\mu$M (3) | >100 |
| NU6013 | 2-amino-6-(2-tetrahydro-furanyl)-methyloxypurine<br>C$_{10}$H$_{13}$N$_5$O$_2$<br>MW = 235.24 | 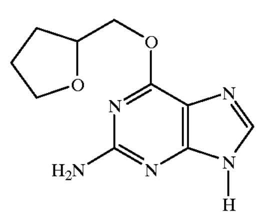 | 48 ± 7% at 100 $\mu$M | >500<br>39 ± 5 at 100 $\mu$M (3) | 261 |
| NU6014 | 2-amino-6-adamantyl-methyloxypurine<br>C$_{16}$H$_{21}$N$_5$O<br>MW = 299.37 | 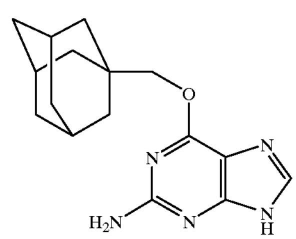 | 61% at 10 $\mu$M | >100 Insol at 100 $\mu$M<br>20 ± 4 at 10 $\mu$M (3) | >100 |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU6017 | C$_{17}$H$_{23}$N$_5$O$_6$<br>MW = 393.39 | 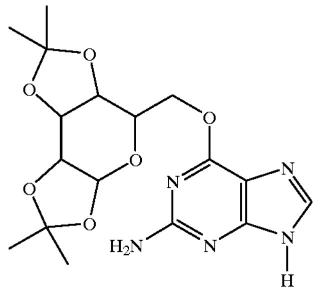 | 10 ± 6% at 100 $\mu$M | >100<br>3 ± 7 at 100 $\mu$M<br>(3) | >100 |
| NU6018 | 2-amino-6-(2-naphthyl)-methyloxypurine<br>C$_{16}$H$_{13}$N$_5$O<br>MW = 291.31 | 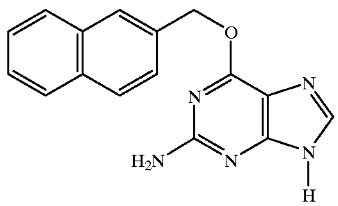 | 12 ± 4% at 10 $\mu$M | >100<br>Insol at 100 $\mu$M<br>9 ± 9 at 10 $\mu$M (3) | >100 |
| NU6019 | 2-amino-6-(2-tetrahydropyranyl)-methyloxypurine<br>C$_{11}$H$_{15}$N$_5$O$_2$<br>MW = 249.27 | 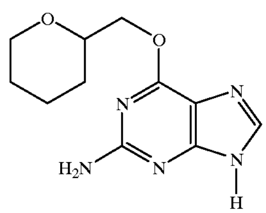 | 51 ± 4% at 100 $\mu$M | >100<br>44 ± 2 at 100 $\mu$M<br>(3) | >100* |
| NU6020 | 2-amino-6-(1-naphthyl)-methyloxypurine<br>C$_{16}$H$_{13}$N$_5$O<br>MW = 291.31 | 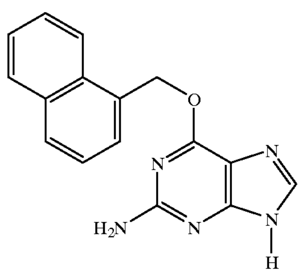 | 10 ± 4% at 10 $\mu$M | >100<br>Insol at 100 $\mu$M<br>3 ± 4 at 10 $\mu$M (3) | >100 |
| NU6021 | 2-amino-6-(2,3-dihydroxypropoxy)purine acetonide<br>C$_{11}$H$_{15}$N$_5$O$_3$<br>MW = 265.27 | 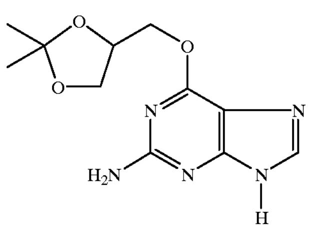 | 36 ± 9% at 100 $\mu$M | >100<br>35 ± 6 at 100 $\mu$M<br>(3) | |
| NU6022 | O$^6$-(1,4-dioxaspiro[4,5]decone-2-methoxyguanine<br>C$_{14}$H$_{19}$N$_5$O$_3$<br>MW = 305.33 | 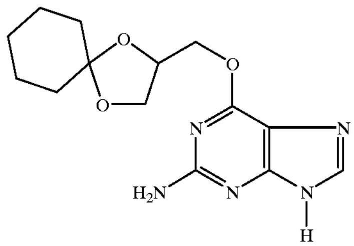 | 26 ± 6% at 100 $\mu$M | >100<br>27 ± 4 at 100 $\mu$M<br>(3) | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU6023 | 2-amino-6-cyclohexylethyl-oxypurine<br>C$_{13}$H$_{19}$N$_5$O<br>MW = 261.32 | 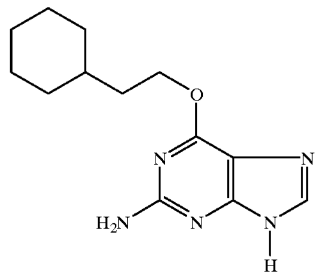 | 68 ± 6% at 100 $\mu$M | >100*<br>58 ± 6 at 100 $\mu$M (3)<br>47.6 | 69 |
| NU6024 | 2-amino-6-[(R)-2',2'-dimethyl-1',3'-dioxolane-5'-methyl]oxypurine<br>C$_{11}$H$_{15}$N$_5$O$_3$<br>MW = 265.27 | 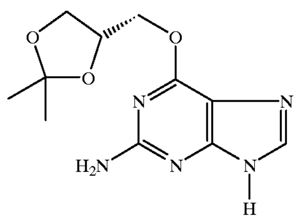 | 50 ± 1% at 100 $\mu$M | 38 ± 3 at 100 $\mu$M (3) | |
| NU6025 | 2-amino-6-[(S)-2',2'-diemthyl-1',3'-dioxolane-5'-methyl]oxypurine<br>C$_{11}$H$_{15}$N$_5$O$_3$<br>MW = 265.27 | 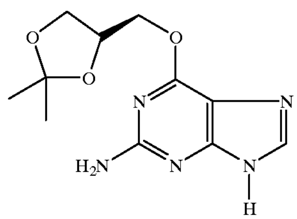 | 34 ± 2% at 100 $\mu$M | >100<br>28 ± 4 at 100 $\mu$M (3) | |
| NU6026 | 6-hydroxymethyl-1,4-benzodioxanguanine<br>C$_{14}$H$_{13}$N$_5$O$_3$<br>MW = 299.28 | 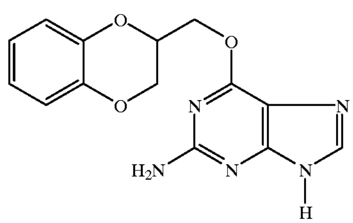 | 52 ± 2% at 100 $\mu$M | >100<br>96 at 100 $\mu$M<br>12, 9 at 10 $\mu$M | >100* |
| NU6027 | 2,6-diamino-4-cyclohexyl-methyloxy-5-nitroso-pyrimidine<br>C$_{11}$H$_{15}$N$_5$O$_3$<br>MW = 251.28 | 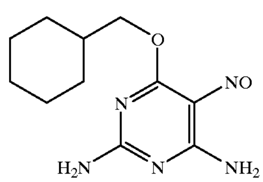 | 67 ± 2% at 10 $\mu$M | >100*<br>Insol at 100 $\mu$M<br>69 ± 10 at 10 $\mu$M (3)<br>1.6 | 8<br>22 |
| NU6028 | 2-amino-6-α-methyl-cyclohexylmethyloxypurine<br>C$_{13}$H$_{19}$N$_5$O<br>MW = 261.32 | 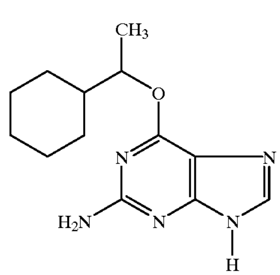 | | | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU6029 | 2-amino-6-(3'-pyridyl)-methyloxypurine<br>C$_{11}$H$_{10}$N$_6$O<br>MW = 242.24 | 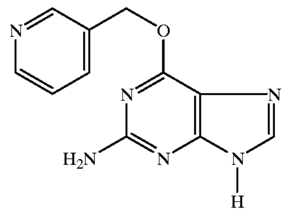 | 56 ± 4 at 100 $\mu$M | 43 ± 4 at 100 $\mu$M (3) | |
| NU6030 | C$_{14}$H$_{19}$N$_5$O<br>MW = 273.33 | 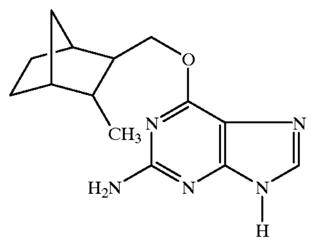 | | | |
| NU6031 | O$^6$-(S)-5-hydroxymethyl-2-pyrrolidinone guanine<br>C$_{10}$H$_{12}$N$_6$O$_2$<br>MW = 248.24 | 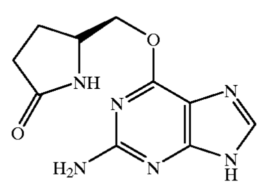 | 26 ± 3% at 100 $\mu$M | 314<br>20 ± 2 at 100 $\mu$M (3) | >1000* |
| NU6032 | O$^6$-(R)-5-hydroxymethyl-2-pyrrolidinone guanine<br>C$_{10}$H$_{12}$N$_6$O$_2$<br>MW = 248.24 | 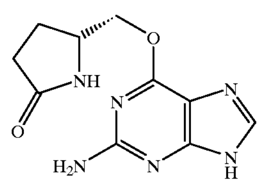 | 54 ± 2% at 100 $\mu$M | 123<br>37 ± 2 at 100 $\mu$M (3) | >1000* |
| NU6033 | 2-amino-6-cyclohexyl-methoxy-8-oxopurine<br>C$_{12}$H$_{17}$N$_5$O$_2$<br>MW = 263.29 | 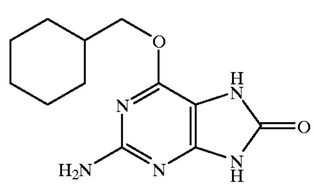 | insol. at 10 $\mu$M | | |
| NU6034 | 2,6-diamino-4(cyclohexylmethoxy)-pyrimidine<br>C$_{11}$H$_{18}$N$_4$O<br>MW = 222.29 | 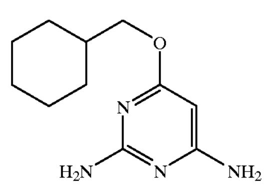 | 4 ± 5 at 10 $\mu$M | Insol at 100 $\mu$M<br>7 ± 3 at 10 $\mu$M (3) | |
| NU6035 | 2,5,6-triamino-4(cyclohexylmethoxy)-pyrimidine<br>C$_{11}$H$_{19}$N$_5$O<br>MW = 237.30 | 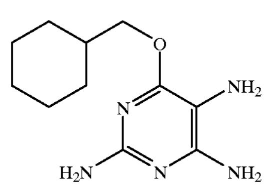 | 40 ± 4 at 100 $\mu$M | 54 ± 8 at 100 $\mu$M (3) | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU6037 | C$_{17}$H$_{21}$ClN$_6$O<br>MW = 360.84 | 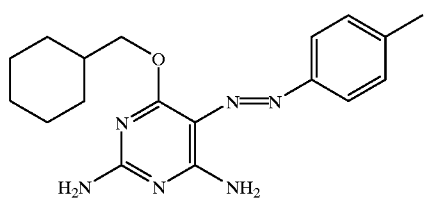 | 3 ± 3 at 10 $\mu$M | Insol at 100 $\mu$M<br>6 ± 4 at 10 $\mu$M (3) | |
| NU6038 | 2,6-diamino-4-(benzyl)pyrimidine<br>C$_{11}$H$_{12}$N$_4$O<br>MW = 216.24 | 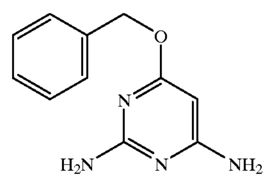 | 3 ± 3 at 100 $\mu$M | 0 ± 7 at 100 $\mu$M (3) | |
| NU6039 | 2,6-diamino-4-(benzylmethoxy)<br>5-nitrosopyrimidine<br>C$_{11}$H$_{11}$N$_5$O$_2$<br>MW = 245.24 | 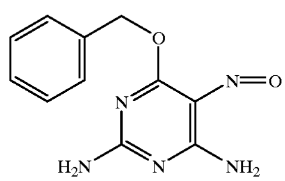 | 54 ± 9 at 100 $\mu$M | 51 ± 2 at 100 $\mu$M (3) | |
| NU6040 | 2,5,6-triamino-4-(benzylmethoxy) pyrimidine<br>C$_{11}$H$_{13}$N$_5$O<br>MW = 231.25 | 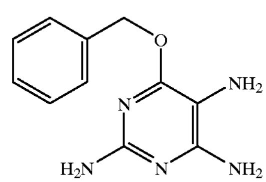 | 4 ± 7 at 100 $\mu$M | 6 ± 10 at 100 $\mu$M (3) | |
| NU6041 | C$_{12}$H$_{20}$N$_4$O<br>MW = 236.31 | 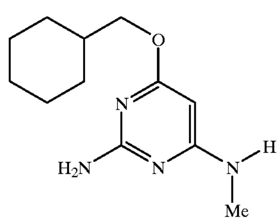 | | | |
| NU6042 | 2-amino-4-chloro-6-methylamino pyrimidine<br>C$_5$H$_7$ClN$_4$<br>MW = 158.59 | 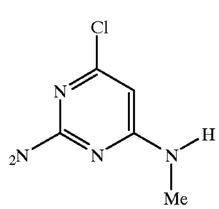 | 3 ± 2 at 100 $\mu$M | 14 ± 24 at 100 $\mu$M (3) | |
| NU6043 | C$_{12}$H$_{11}$N$_5$O$_2$<br>MW = 257.25 | 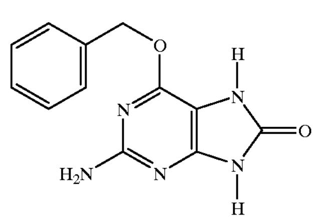 | 13 ± 9 at 100 $\mu$M | 8 ± 13 at 100 $\mu$M (3) | |

TABLE 1-continued

| Number | Name | Structure | IC$_{50}$ ($\mu$M) or % inhibition | | |
|---|---|---|---|---|---|
| | | | CDK1 | CDK2 | CDK4 |
| NU6044 | C$_{11}$H$_{17}$N$_5$O<br>MW = 235.28 | 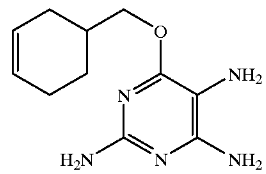 | | | |
| NU6045 | 2,6-diamino-4(cyclohexenyl)-5-nitrosopyrimidine<br>C$_{11}$H$_{15}$N$_5$O$_2$<br>MW = 249.27 | 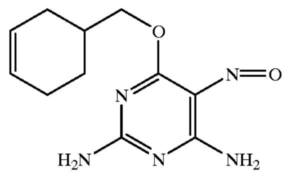 | 73 ± 3 at 10 $\mu$M | Insol at 100 $\mu$M<br>70 ± 1 at 10 $\mu$M (3)<br>6.1 | |
| NU6046 | 2,6-diamino-4-(cylcohenyl)pyrimidine<br>C$_{11}$H$_{16}$N$_4$O<br>MW = 220.27 | 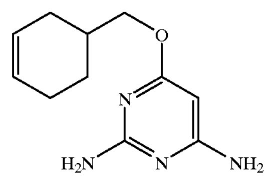 | 16 ± 13 at 100 $\mu$M | 8 ± 1 at 100 $\mu$M (3) | |
| NU6047 | 2-chloro-6-cyclohexylmethoxypurine<br>C$_{12}$H$_{15}$ClN$_4$O<br>MW = 266.73 | 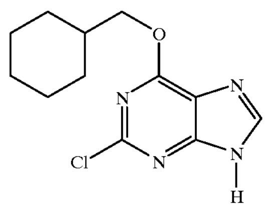 | 100 $\mu$M - Insol<br>10 $\mu$M = 6 ± 4 (3) | Insol at 100 $\mu$M<br>5 ± 3 at 10 $\mu$M (3) | |
| NU6048 | 2-dimethylamino-6-cyclohexyl methoxypurine<br>C$_{14}$H$_{21}$N$_5$O<br>MW = 275.35 | 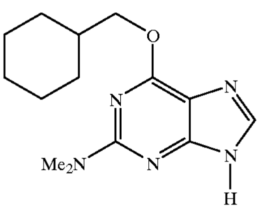 | 100 $\mu$M - Insol<br>10 $\mu$M = 27 ± 6 (3) | Insol at 100 $\mu$M<br>31 ± 3 at 10 $\mu$M (3) | |

What is claimed is:

1. A method for the treatment of a tumour or other cell proliferation disorder in a mammal which comprises administering to said mammal an effective antitumour and cyclic dependent kinase-inhibiting amount of a purine compound having the structural formula I

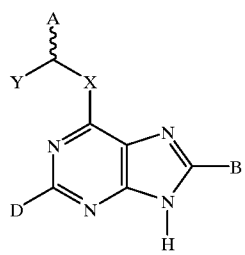

I or a pharmaceutically acceptable salt thereof, wherein
X is O, S or CH$_2$
D is halo or NZ$_1$Z$_2$
where Z$_1$ and Z$_2$ are each independently H, C$_{1-4}$ alkyl or C$_{1-4}$ hydroxyalkyl;
A is selected from the group consisting of H, C$_{1-4}$ alkyl, C$_{1-4}$ alkoxy, hydroxy, CH$_2$(CH$_2$)$_n$OH(n=1–4), and NR$_{a1}$R$_{a2}$ where R$_{a1}$ and R$_{a2}$ are each independently H or C$_{1-4}$ alkyl;
B is selected from the group consisting of H, C$_{1-4}$ alkyl, C$_{1-4}$ alkoxy, CF$_3$, an optionally substituted aryl or an optionally substituted aralkyl and a hydroxy or oxo group; and
Y is an optionally substituted 5- or 6-membered cycloalkane or cycloalkene ring having one or two double bonds or heterocyclic ring; or a linear or branched hydrocarbon chain optionally substituted by hydroxyl or alkoxy.

2. The method of claim 1 wherein Y is a cycloalkane ring or a cycloalkene ring of one or two double bonds or a heterocyclic ring which is hydroxy substituted.

3. The method of claim 1 wherein Y is a 5- or 6-membered cycloalkane or a cycloalkene ring having one or two double bonds.

4. The method of claim 3 wherein one or two of the carbon atoms in the cycloalkane or cycloalkene ring are replaced by hetero atoms.

5. The method of claim 4 wherein said hetero atoms or groups are selected from the group consisting of —N=, S, O and NR' (where R' is H or $C_{1-4}$ alkyl).

6. The method of claim 1 wherein Y is a substituted 5- to 6-membered cycloalkane or cycloalkene ring having one or two double bonds or a substituted heterocyclic ring and the substituent is selected from the group consisting of $C_{1-4}$ alkyl, OH, $C_{1-4}$ alkoxy, halogen, $CF_3$, CN, $N_3$ and $NR_{y1}R_{y2}$ where $R_{y1}$ and $R_{y2}$ are each independently H or $C_{1-4}$ alkyl.

7. The method of claim 6 wherein two of said Y substituents are on adjacent atoms of the ring and are linked to form an additional fused ring structure.

8. The method of claim 7 wherein Y is a ring structure represented by one of the following structural formulae:

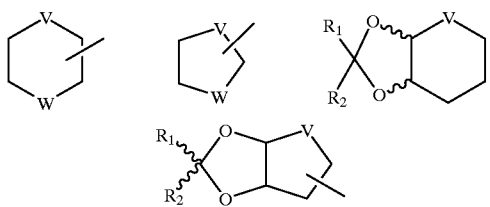

wherein V and W are each selected independently from

O, S, NR' (R' is H or $C_{1-4}$ alkyl)

And $CH_2$ or =CH; and $R_1$ and $R_2$ are each H or $C_{1-4}$ alkyl.

9. The method of claim 1 wherein D is an unsubstituted amino group and X is oxygen.

10. The method of claim 1 wherein the purine compound is selected from the group consisting of:

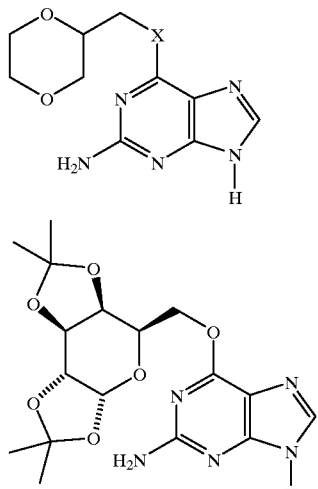

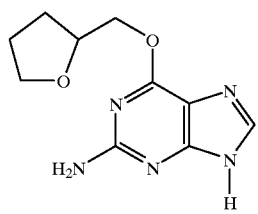

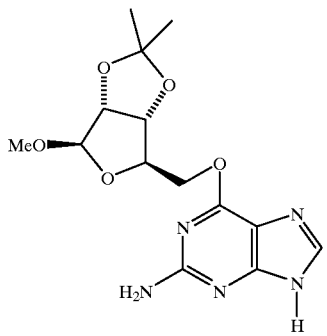

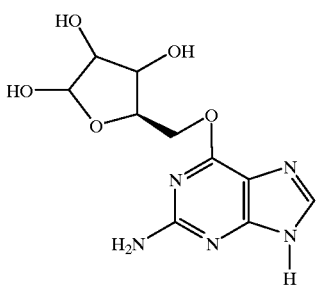

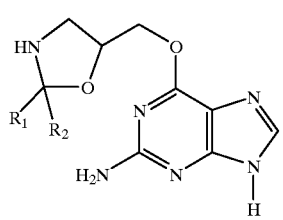

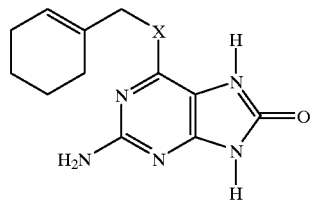

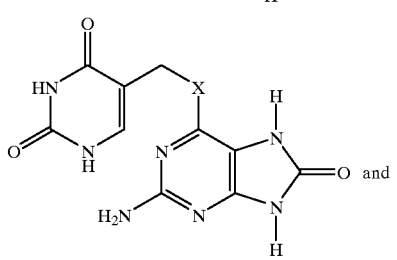

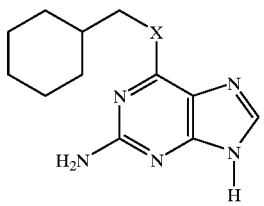

X = O or S
$R_1$ = H, $CH_3$ or $C_2H_5$
$R_2$ = H, $CH_3$ or $C_2H_5$

11. The method of claim 1 wherein the optional alkoxy substituent of Y has 1–6 carbon atoms.

12. The method of claim 1 wherein said purine compound is one of the following:

2-amino-6-(3-methyl-2-oxo)butyloxypurine ethylene acetal 2-amino-6-cyclohexyl-methyloxypurine
(O⁶-cyclohexylmethylguanine)
2-amino-6-cyclopentyl-methyloxypurine
(O⁶-cyclopentylmethylguanine)
2-amino-6-cyclohex-3-enylmethyloxypurine
2-amino-6-cyclopent-1-enylmethyloxypurine
(O⁶-Cyclohexenylmethylguanine)
2-amino-6-perillyloxymethylpurine
O⁶-Ribofuranoxylguanine
2-amino-6-(2-tetrahydro-furanyl)-methyloxypurine
2-amino-6-adamantyl-methyloxypurine
O⁶-Galactoxylguanine
2-amino-6-(2-naphthyl)-methyloxypurine
2-amino-6-(2-tetrahydropyranyl)-methyloxypurine
2-amino-6-(1-naphthyl)-methyloxypurine
O⁶-(2,2-Dimethyl-1,3-dioxolane-4-methoxy)guanine
O⁶(1,4-Dioxaspirol[4.5]decane-2-methoxy)guanine.

13. A purine compound selected from the group consisting of:
O⁶-Ribofuranosylguanine
2-amino-6-(2-tetrahydro-furanyl)-methyloxypurine
2-amino-6-adamantyl-methyloxypurine
O⁶-Galactoxylguanine
2-amino-6-(2-naphthyl)-methyloxypurine
2-amino-6-(2-tetrahydropyranyl)-methyloxypurine
2-amino-6-(1-naphthyl)-methyloxypurine
O⁶-(2,2-Dimethyl-1,3-dioxolane-4-methoxy)guanine
O⁶(1,4-Dioxaspirol[4.5]decane-2-methoxy)guanine
and pharmaceutically acceptable salts thereof.

14. A pharmaceutical composition consisting essentially of an effective tumour cell proliferation inhibiting amount of a purine compound in unit dosage form together with a pharmaceutically acceptable carrier, said purine compound having the formula I

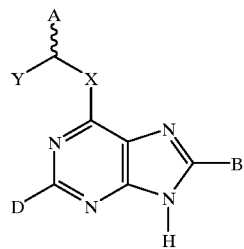

I or a pharmaceutically acceptable salt thereof, wherein
X is O, S or $CH_2$
D is halo or $NZ_1Z_2$
where $Z_1$ and $Z_2$ are each independently H, $C_{1-4}$ alkyl or $C_{1-4}$ hydroxyalkyl;
A is selected from the group consisting of H, $C_{1-4}$ alkyl, $C_{1-4}$ alkoxy, hydroxy, $CH_2(CH_2)_nOH(n=1-4)$, and $NR_{a1}R_{a2}$ where $R_{a1}$ and $R_{a2}$ are each independently H or $C_{1-4}$ alkyl;
B is selected from the group consisting of H, $C_{1-4}$ alkyl, $C_{1-4}$ alkoxy, $CF_3$, an optionally substituted aryl or an optionally substituted aralkyl and a hydroxy or oxo group; and
Y is an optionally substituted 5- to 6-membered cycloalkane or cycloalkene ring having one or two double bonds or an optionally substituted heterocyclic ring; or a linear or branched hydrocarbon chain optionally substituted by hydroxyl or alkoxy.

15. A pharmaceutical composition for treatment of tumours or other cell proliferation disorders in mammals, said composition comprising as the active therapeutic ingredient, an effective antitumour and cyclic dependent kinase-inhibiting amount of a purine compound having the structural formula I below:

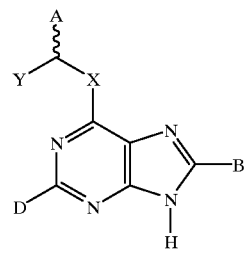

I wherein
X is O, S or $CH_2$;
D is halo or $NZ_1Z_2$
where $Z_1$ and $Z_2$ are each independently H or $C_{1-4}$ alkyl or $C_{1-4}$ hydroxyalkyl;
A is selected from H, $C_{1-4}$ alkyl, $C_{1-4}$ alkoxy, hydroxy, $CH_2(CH_2)_nOH(n=1-4)$, and $NR_{a1}R_{a2}$ where $R_{a1}$ and $R_{a2}$ are each independently H or $C_{1-4}$ alkyl;
B is selected from H, $C_{1-4}$ alkyl, $C_{1-4}$ alkoxy, $CF_3$, an optionally substituted aryl or an optionally substituted aralkyl, and a hydroxy or oxo group; and
Y is an optionally substituted 5- to 6-membered cycloalkane or cycloalkene having one or two double bonds or an optionally substituted heterocyclic ring
or a pharmaceutically acceptable salt of said purine compound, admixed with at least one other compatible pharmaceutically acceptable additive, carrier, diluent or excipient.

* * * * *